United States Patent
Dreyfus et al.

(10) Patent No.: US 8,292,903 B2
(45) Date of Patent: Oct. 23, 2012

(54) SUTURE PASSER

(75) Inventors: Peter Dreyfus, Miami, FL (US);
Reynaldo Sylvester, Miami, FL (US);
Barry N. Gellman, North Easton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 109 days.

(21) Appl. No.: 12/829,625

(22) Filed: Jul. 2, 2010

(65) Prior Publication Data

US 2010/0268256 A1 Oct. 21, 2010

Related U.S. Application Data

(63) Continuation of application No. 11/255,615, filed on Oct. 20, 2005, now Pat. No. 7,771,438, which is a continuation of application No. 09/861,826, filed on May 21, 2001, now Pat. No. 6,997,932.

(51) Int. Cl.
*A61B 17/10* (2006.01)

(52) U.S. Cl. ................................................ 606/139

(58) Field of Classification Search .............. 606/139, 606/144–148
See application file for complete search history.

(56) References Cited

U.S. PATENT DOCUMENTS

| | | | |
|---|---|---|---|
| 1,037,864 A | 9/1912 | Carlson et al. |
| 1,449,087 A | 3/1923 | Bugbee |
| 1,815,725 A | 7/1931 | Pilling et al. |
| 1,822,330 A | 9/1931 | Ainslie |
| 1,981,651 A | 11/1934 | Logan |
| 2,240,330 A | 4/1941 | Flagg |
| 3,013,559 A | 12/1961 | Thomas |
| 3,090,386 A | 5/1963 | Curtis |
| 3,160,157 A | 12/1964 | Chisman |
| 3,470,875 A | 10/1969 | Johnson |
| 3,638,653 A | 2/1972 | Berry |
| 3,799,169 A | 3/1974 | Beroff et al. |
| 3,840,017 A | 10/1974 | Violante |
| 3,946,740 A | 3/1976 | Bassett |
| 4,224,947 A | 9/1980 | Fukuda |
| 4,345,601 A | 8/1982 | Fukuda |
| 4,373,530 A | 2/1983 | Kilejian |
| 4,406,237 A | 9/1983 | Eguchi et al. |
| 4,417,532 A | 11/1983 | Yasukata |
| 4,596,249 A | 6/1986 | Freda et al. |
| 4,621,640 A | 11/1986 | Mulhollan et al. |
| 4,890,615 A | 1/1990 | Caspari et al. |
| 4,957,498 A | 9/1990 | Caspari et al. |
| 5,085,661 A | 2/1992 | Moss |
| 5,100,418 A | 3/1992 | Yoon et al. |
| 5,152,769 A | 10/1992 | Baber |
| 5,181,919 A | 1/1993 | Bergman et al. |
| 5,312,436 A | 5/1994 | Coffey et al. |
| 5,350,385 A | 9/1994 | Christy |
| 5,364,408 A | 11/1994 | Gordon |
| 5,387,221 A | 2/1995 | Bisgaard |

(Continued)

FOREIGN PATENT DOCUMENTS

EP 0589409 A1 3/1994

(Continued)

*Primary Examiner* — Anu Ramana
(74) *Attorney, Agent, or Firm* — Brown Rudnick LLP

(57) ABSTRACT

A device for placing one or more sutures and approximating tissue includes an elongate body member and a suture deployment system. The suture deployment system includes a suture carrier with a sharpened end for piercing tissue.

16 Claims, 23 Drawing Sheets

U.S. PATENT DOCUMENTS

| | | | |
|---|---|---|---|
| 5,389,103 A | 2/1995 | Melzer et al. |
| 5,417,699 A | 5/1995 | Klein et al. |
| 5,454,823 A | 10/1995 | Richardson et al. |
| 5,458,609 A | 10/1995 | Gordon et al. |
| 5,470,338 A | 11/1995 | Whitfield et al. |
| 5,474,565 A | 12/1995 | Trott |
| 5,520,703 A | 5/1996 | Essig et al. |
| 5,522,820 A | 6/1996 | Caspari et al. |
| 5,527,321 A | 6/1996 | Hinchliffe |
| 5,540,704 A | 7/1996 | Gordon et al. |
| 5,571,119 A | 11/1996 | Atala |
| 5,573,540 A | 11/1996 | Yoon |
| 5,573,542 A | 11/1996 | Stevens |
| 5,575,800 A | 11/1996 | Gordon |
| 5,578,044 A | 11/1996 | Gordon et al. |
| 5,591,179 A | 1/1997 | Edelstein |
| 5,613,975 A | 3/1997 | Christy |
| 5,632,752 A | 5/1997 | Buelna |
| 5,653,717 A | 8/1997 | Ko et al. |
| 5,662,663 A | 9/1997 | Shallman |
| 5,662,664 A | 9/1997 | Gordon et al. |
| 5,662,666 A | 9/1997 | Onuki et al. |
| 5,665,096 A | 9/1997 | Yoon |
| 5,700,272 A | 12/1997 | Gordon et al. |
| 5,713,910 A | 2/1998 | Gordon et al. |
| 5,741,276 A | 4/1998 | Poloyko et al. |
| 5,741,277 A | 4/1998 | Gordon et al. |
| 5,741,278 A | 4/1998 | Stevens |
| 5,741,279 A | 4/1998 | Gordon et al. |
| 5,755,727 A | 5/1998 | Kontos |
| 5,766,186 A | 6/1998 | Faraz et al. |
| 5,776,148 A | 7/1998 | Christy |
| 5,776,152 A | 7/1998 | Sekons |
| 5,817,108 A | 10/1998 | Poncet |
| 5,817,110 A | 10/1998 | Kronner |
| 5,855,585 A | 1/1999 | Kontos |
| 5,871,488 A | 2/1999 | Tovey et al. |
| 5,879,371 A | 3/1999 | Gardiner et al. |
| 5,908,426 A | 6/1999 | Pierce |
| 5,908,428 A | 6/1999 | Scirica et al. |
| 5,919,199 A | 7/1999 | Mers Kelly et al. |
| 5,964,773 A | 10/1999 | Greenstein |
| 5,980,538 A | 11/1999 | Fuchs et al. |
| 6,048,351 A | 4/2000 | Gordon et al. |
| 6,051,006 A | 4/2000 | Shluzas et al. |
| 6,071,292 A | 6/2000 | Makower et al. |
| 6,096,051 A | 8/2000 | Kortenbach et al. |
| 6,346,111 B1 * | 2/2002 | Gordon et al. | 606/144 |
| 6,475,135 B1 * | 11/2002 | Levy | 600/30 |
| 6,997,932 B2 | 2/2006 | Dreyfuss et al. |
| 7,033,370 B2 | 4/2006 | Gordon et al. |

FOREIGN PATENT DOCUMENTS

| | | |
|---|---|---|
| EP | 0668056 A1 | 8/1995 |
| WO | WO-92/12674 A1 | 8/1992 |
| WO | WO-93/01750 A1 | 2/1993 |
| WO | WO-94/13211 A1 | 6/1994 |
| WO | WO-96/27331 A1 | 9/1996 |

* cited by examiner

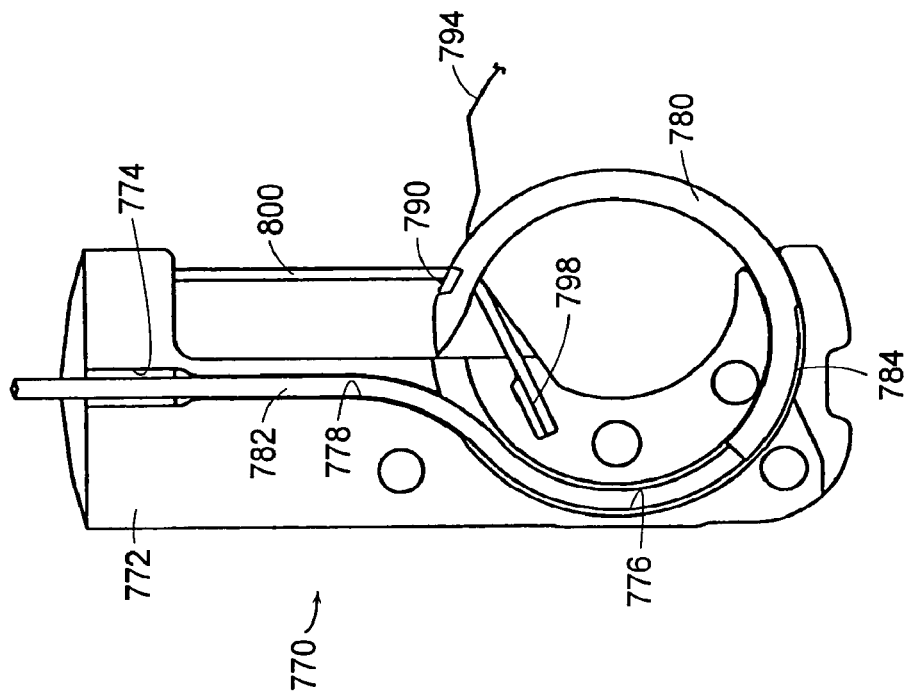
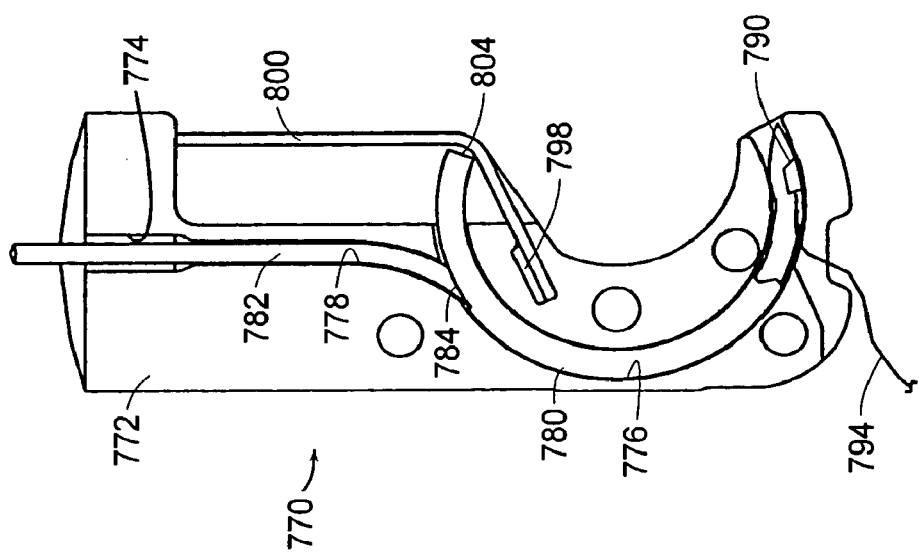

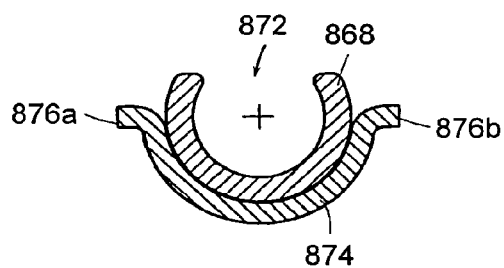 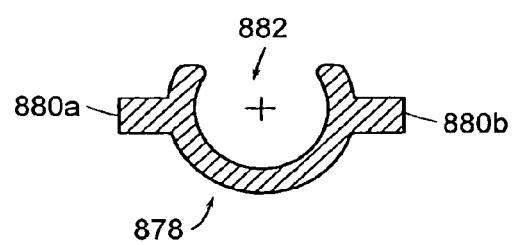
FIG. 11A              FIG. 11B
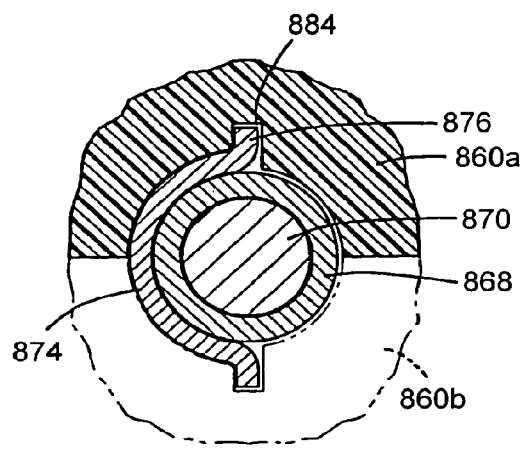
FIG. 12
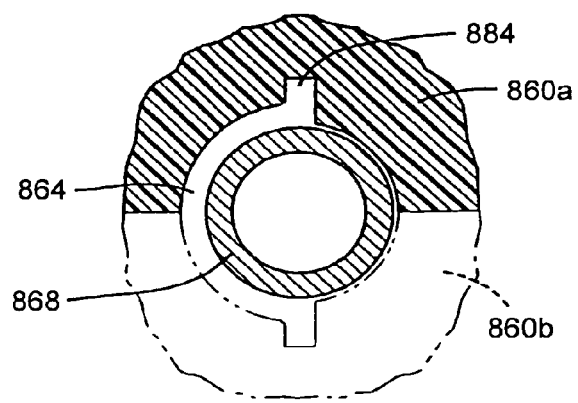
FIG. 13

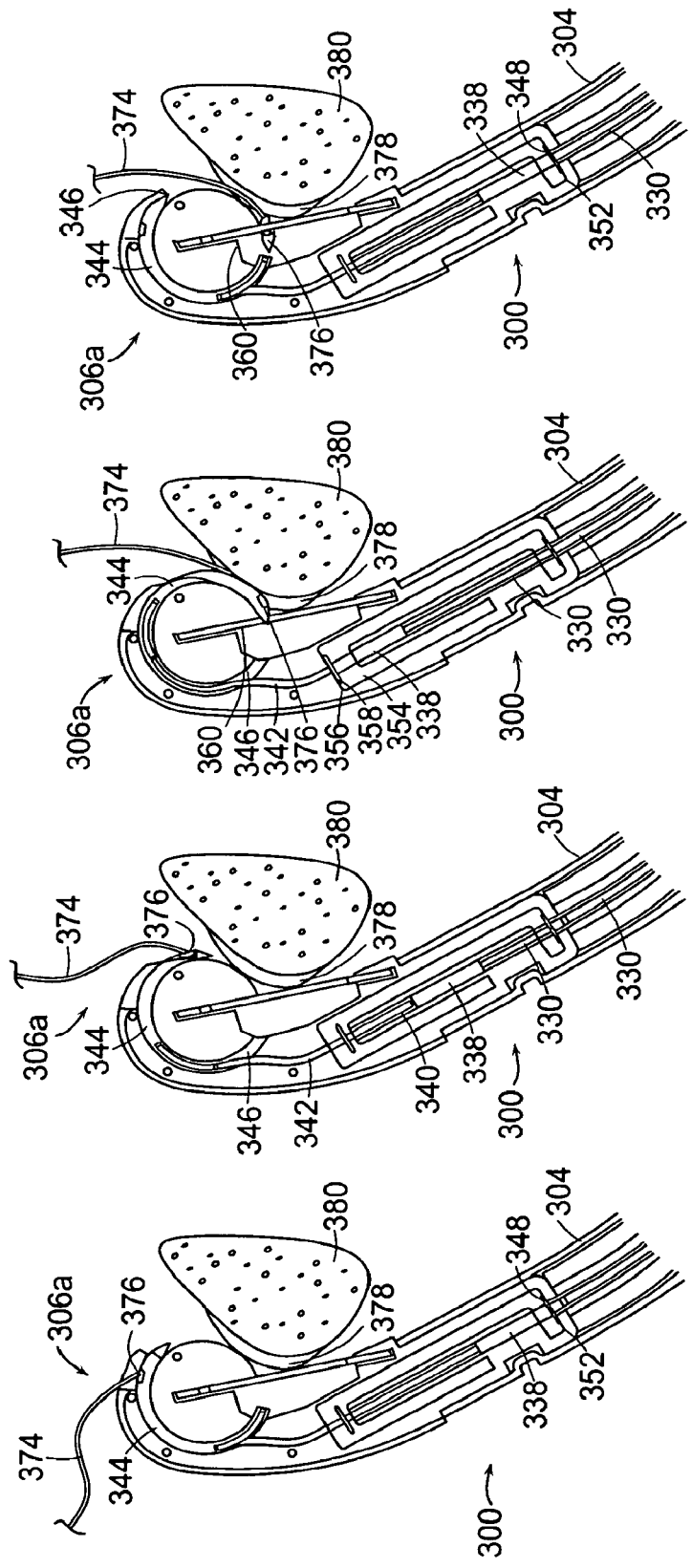

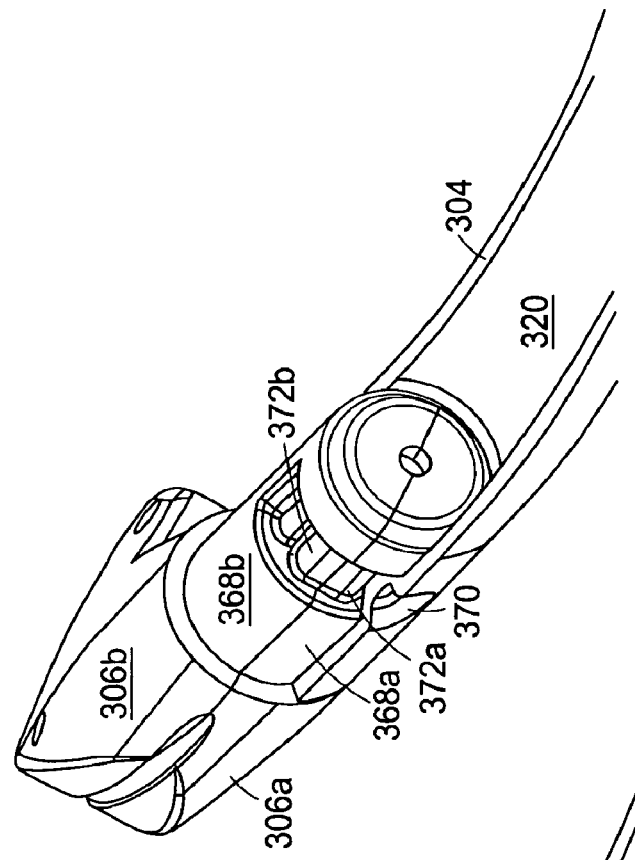
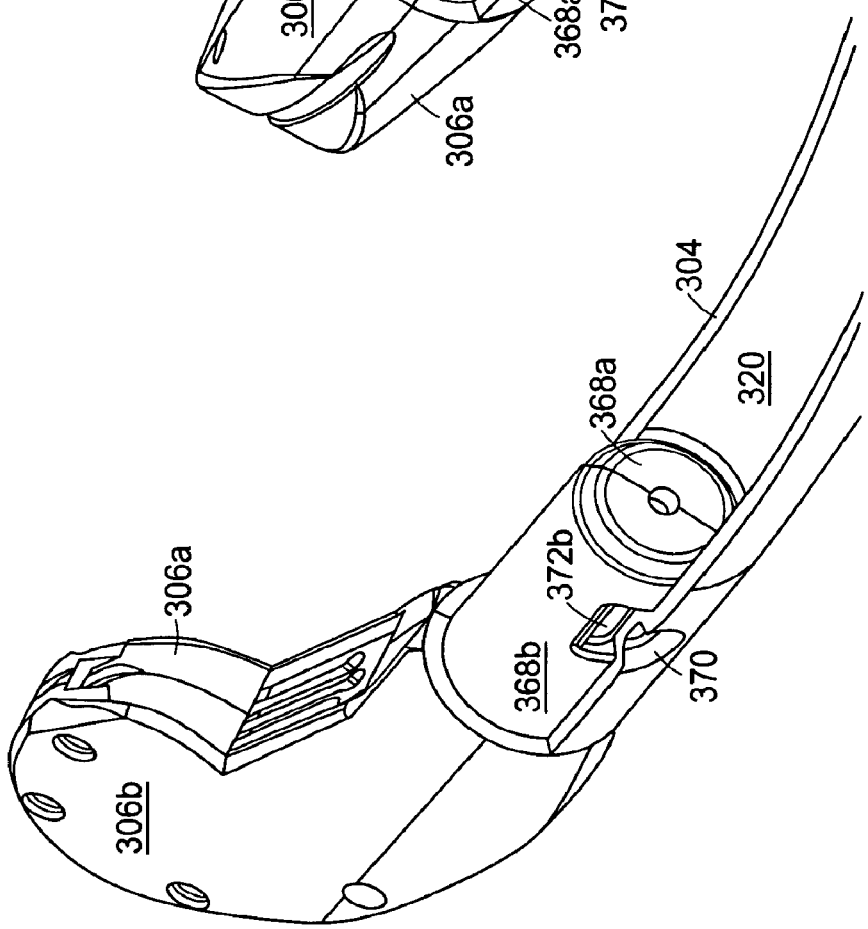
FIG. 18B
FIG. 18A

SUTURE PASSER

CROSS-REFERENCE TO RELATED CASES

This claims priority to and is a continuation of allowed patent application Ser. No. 11/255,615 filed on Oct. 20, 2005, which itself claims priority to and is a continuation of U.S. Pat. No. 6,997,932. U.S. Pat. No. 6,997,932 issued on Feb. 14, 2006, from patent application Ser. No. 09/861,826 filed on May 21, 2001. The entirety of each of these related cases is incorporated herein by reference.

TECHNICAL FIELD

The invention relates to devices and methods for placing sutures.

BACKGROUND INFORMATION

Suturing of body tissue is a time consuming aspect of many surgical procedures. For many surgical procedures, it is necessary to make a large opening in the human body to expose the area that requires surgical repair. There are instruments available that allow for viewing of certain areas of the human body through a small puncture wound without exposing the entire body cavity. These instruments, called endoscopes, can be used in conjunction with specialized surgical instruments to detect, diagnose, and repair areas of the body that previously required open surgery to access.

Some surgical instruments used in endoscopic procedures are limited by the manner in which they access the areas of the human body in need of repair. In particular, the instruments may not be able to access tissue or organs located deep within the body or that are in some way obstructed. Also, many of the instruments are limited by the way they grasp tissue, apply a suture, or recapture the needle and suture. In addition, the needle can become separated from the needle-driving device and lost within a patient. Furthermore, many of the instruments are complicated and expensive to use due to the numerous parts and/or subassemblies required to make them function properly.

SUMMARY OF THE INVENTION

The suture passer of the present invention eliminates the need for a preassembled needle and suture and eliminates the possibility of needle loss during suturing. This is accomplished by eliminating the use of a loose needle or any needle at all. Specifically, the suture passer uses a suture with a formed tip that engages a suture carrier. The suture carrier is coupled to the suture passer and has a sharpened end for piercing tissue. The suture carrier also has a notch for carrying the formed tip of the suture. When the device is actuated, the suture carrier pierces the tissue and carries the formed tip through the tissue and into a formed tip catch. The suture carrier is then retracted leaving the suture intact.

In one aspect, the invention relates to a suturing instrument. The suturing instrument includes an elongate body member, a suture deployment system disposed at a distal portion of the elongate body member, and a catch to receive and retain a formed suture tip. The suture deployment system includes a suture carrier having a sharpened distal end for tissue penetration and a notch for holding the formed suture tip.

In some embodiments, the suturing instrument may include a deployment controller having a proximal end and a distal end. The deployment controller extends substantially along a longitudinal axis of the elongate body member to the distal portion of the elongate body member, where the distal end of the deployment controller is coupled to the suture carrier and moves the suture carrier between a retracted position and a deployed position. The proximal end of the deployment controller may be coupled to an actuator. In some embodiments, the deployment controller guides the suture carrier along a path that includes a proximal curved path segment such that the suture carrier initially travels away from the elongate body member and then towards the elongate body member.

In another aspect, the invention relates to a suturing instrument including a suture carrier and a body member defining a suture exit port and a suture carrier channel. The suture carrier includes a sharpened distal end for tissue penetration and a notch for holding a formed suture tip. The suture carrier is movably positioned in the suture carrier channel between a retracted position within an interior region of the body member and a deployed position exterior to the body member. The suture carrier is configured within the suture carrier channel such that the suture carrier exits the interior region of the body member through the suture exit port.

In yet another aspect, the invention relates to a suturing instrument including an elongate body member having a longitudinal axis and a distal tip suture deployment assembly joined with a distal end of the elongate body member such that the distal tip assembly is free to rotate axially about the longitudinal axis of the elongate body member. The distal tip suture deployment assembly includes a suture exit port and a curved suture carrier channel formed in the distal tip suture deployment assembly, a curved suture carrier movably positioned in the curved suture carrier channel, a suture with a formed tip coupled to the suture carrier, and a deployment controller including a proximal end and a distal end. The deployment controller extends substantially along the longitudinal axis of the elongate body member to the distal end of the elongate body member, where the distal end of the deployment controller is coupled to the distal tip suture deployment assembly and moves the curved suture carrier through the curved suture carrier channel as the deployment controller moves between a retracted position and a deployed position. Additionally, the proximal end of the deployment controller may be coupled to an actuator.

In still another aspect, the invention relates to a suturing instrument including a body member defining an exit port and a carrier channel, a carrier movably positioned in the carrier channel, and a surgical needle permanently fixed on a distal end of the carrier. The carrier has a retracted position within an interior region of the body member and a deployed position exterior to the body member. The carrier is configured within the carrier channel such that the carrier exits the interior region of the body member through the exit port. The permanently fixed needle may include a notch for holding a formed suture tip. In addition, the exit port, suture carrier channel, and suture carrier can be located in a distal tip assembly coupled to the body member, and the distal tip assembly can be coupled to the body member such that the distal tip assembly is free to rotate axially about a longitudinal axis of the body member.

Various embodiments according to any of the foregoing aspects of the invention can include the following features. A suture can include a formed tip, which may be permanently fixed to an end of the suture. The formed tip of the suture can insert into the suture carrier notch. Also, the formed tip can be plastic, metal, or polymer compound. In addition, the suturing instrument can include a catch to receive and retain the formed suture tip, where the catch is positioned on the body member such that a distal segment of the suture carrier's path is intercepted by the catch. Additionally, the suturing instrument may include a second suture carrier and a second exit port. Further, the deployment controller may be coupled to the suture carrier with a flexible driver member. The flexible driver member may be manufactured of an alloy that includes at least or exclusively nickel and titanium.

An additional aspect of the invention relates to a method for placing a suture in tissue. In accordance with the method, inserting a suturing instrument enclosing a suture carrier having a sharpened end for tissue penetration and a notch for holding a formed suture tip, deploying the suture carrier out of the suturing instrument through an exit port such that the suture carrier exits an interior region of the suturing instrument through the exit port along a path which approaches being substantially tangential to an outer surface of the suturing instrument surrounding the exit port, and capturing a suture carried by the suture carrier in a catch that receives and retains the formed suture tip. The suture carrier is movably positioned within a suture carrier channel adjacent the tissue to be sutured.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings.

FIGS. 6C and 6D are partial cutaway views illustrating the general structure and operation of an alternate embodiment of a suture delivery and capture system.

FIGS. 11A and 11B are cross-sectional views of two alternate designs of the suture carrier taken along line 11-11 of FIG. 9A.

FIG. 12 is a cross-sectional view of the suture carrier and guide track taken along line 12-12 of FIG. 10.

FIG. 13 is a cross-sectional view of the suture carrier and guide track taken along line 13-13 of FIG. 10.

FIGS. 17A-17D are cutaway views illustrating the operation of the embodiment shown in FIGS. 14-16.

FIGS. 18A-18B are partial-cutaway views of the distal tip of one embodiment of a suturing device and illustrating the general structure and operation of the axial articulation of the suture driver head.

DESCRIPTION

Embodiments of the present invention are described below. It is, however, expressly noted that the present invention is not limited to these embodiments, but rather the intention is that modifications that are apparent to the person skilled in the art are also included.

Figures 1A, 1B:
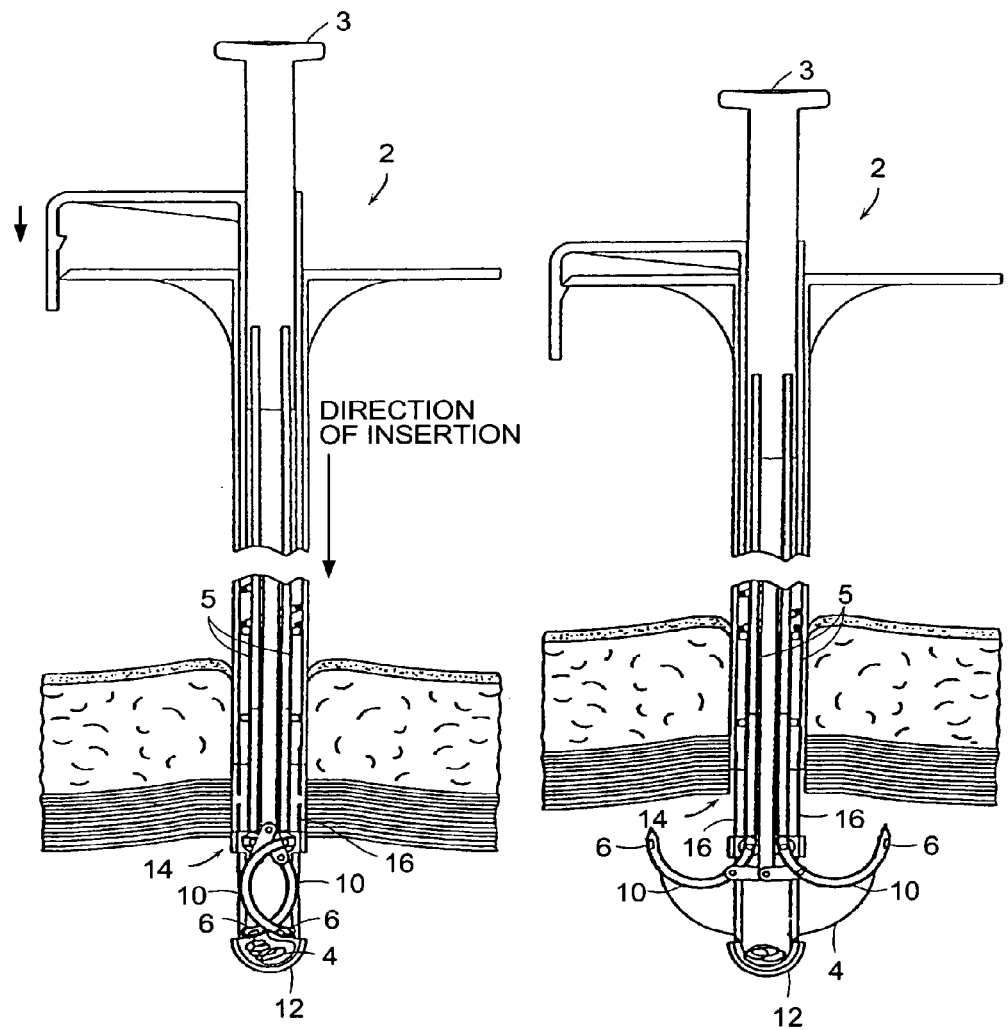
FIGS. 1A-1H are cutaway views illustrating the general structure and operation of one embodiment of the present invention.
Figures 1C, 1D:
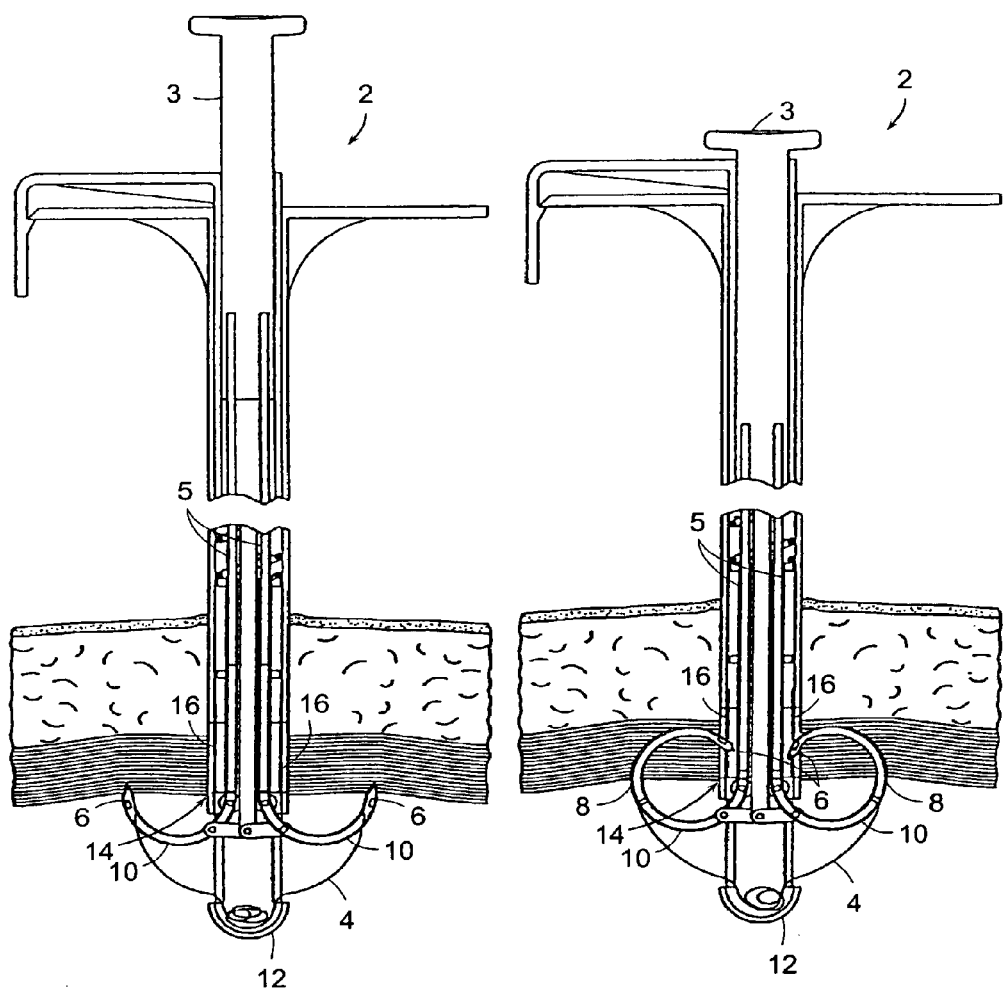
Figures 1E, 1F:
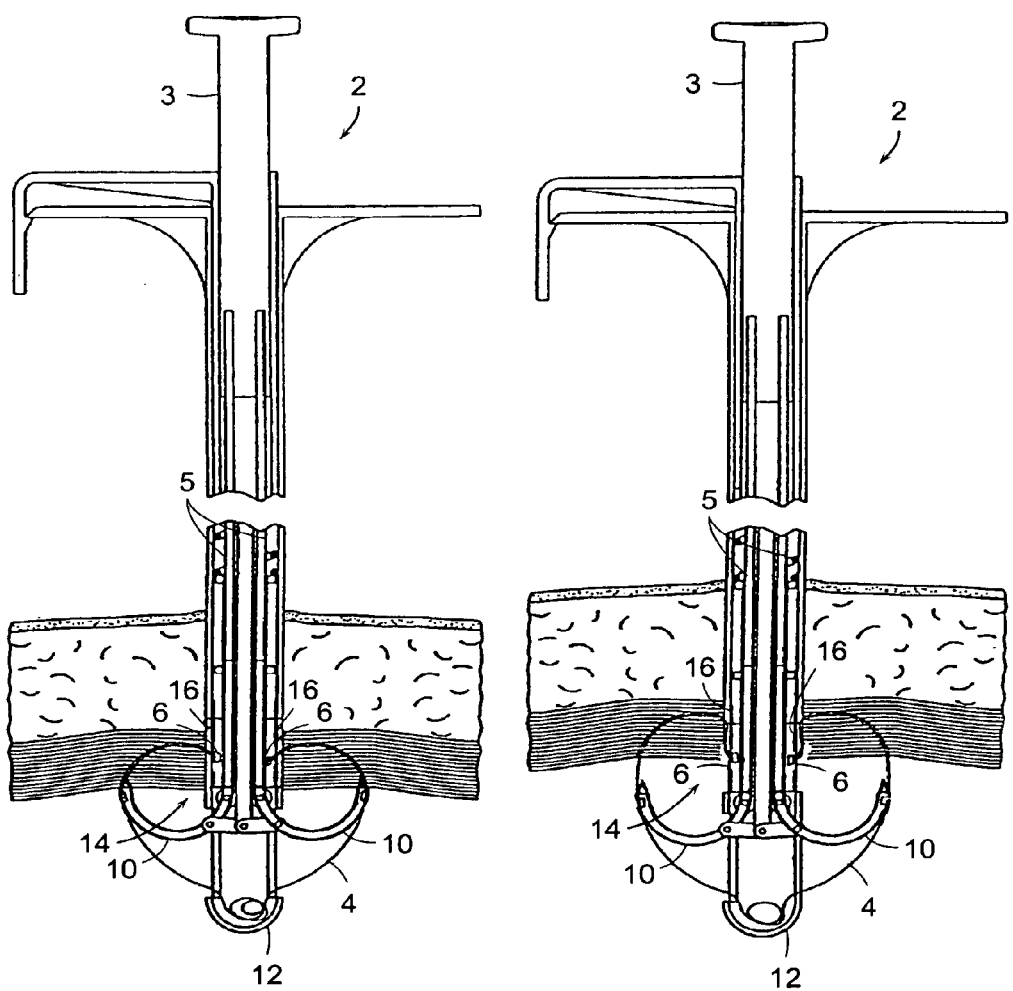
Figure 1G:
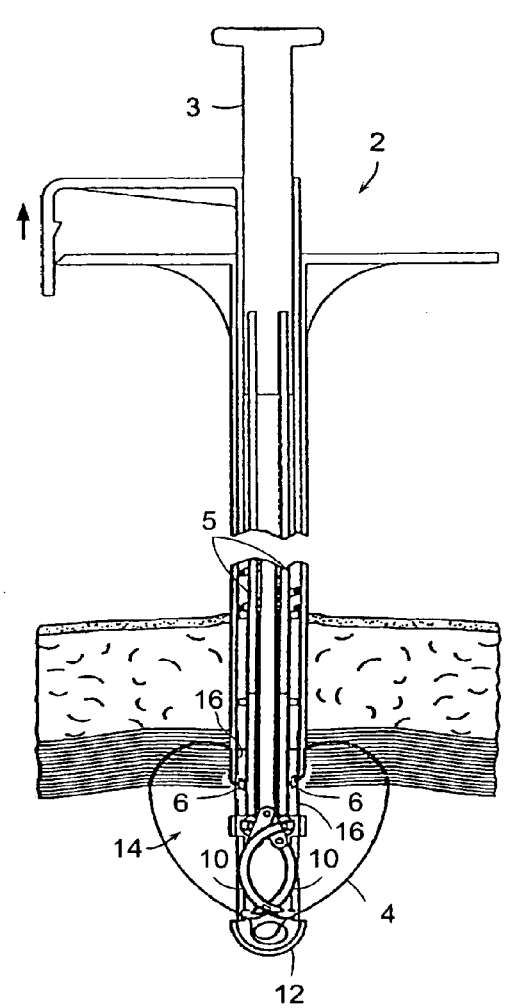
Figure 1H:
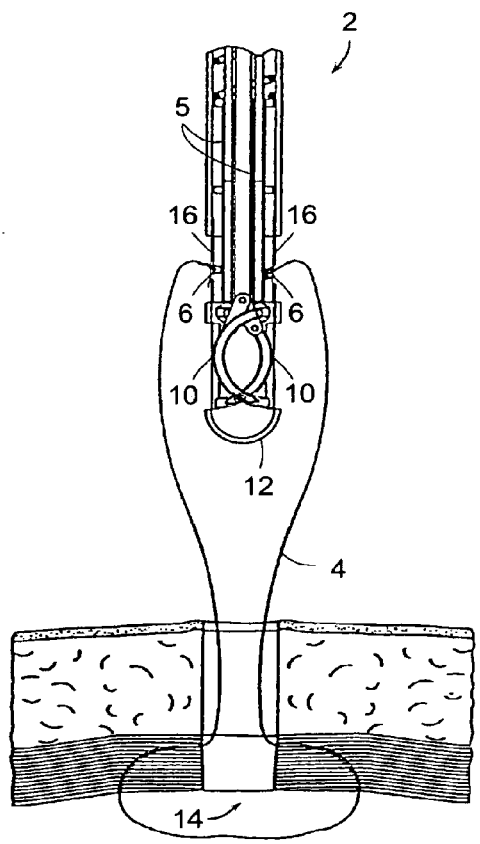

FIGS. 1A-1H illustrate the general structure and operation of one embodiment of the present invention. A device 2 according to the present invention incorporates a length of suture material 4 with a formed tip 6 on each end. Suture carriers 10 hold the formed tips 6. The suture carriers 10 and formed tips 6 are deployable out of a housing 12 and into tissue surrounding a puncture wound 14. Deployment is via an actuator, such as a plunger 3, coupled to a pair of rigid driving members 5, which are suitably attached to the suture carriers 10. In this disclosed embodiment, the plunger 3 is pushed, simultaneously driving the suture carriers 10 and formed tips 6 into a catch mechanism 16. The suture carriers 10 are then retracted back into the housing 12. The housing 12 (now containing only the suture carriers 10 without the formed tips 6) and the catch mechanism 16 with the captured formed tips 6 are retracted as shown in FIGS. 1G and 1H. With a loop of suture 4 having thus been placed in the tissue surrounding the puncture wound 14, the suture device 2 is removed from the wound 14, thereby pulling the ends of the suture 4 with it (FIG. 1H). Closure of the puncture wound 14 is accomplished by cutting the suture 4 to disconnect the formed tips 6 from the installed suture 4, tying a knot with the now-free ends of the installed suture 4, and pushing into the wound 14 the knot and any suture 4 extending out of the wound 14. Superficial closure is then performed by normal means according to a surgeon's preference.

The suture carrier path shown in FIGS. 1A-1H is generally circular; however, it is contemplated that the above embodiment may be modified to include suture carrier paths other than circular, such as helical, elliptical, or straight, by modification of the suture carriers and/or the suture carrier guides defined by the housing 12. It is also possible to adapt the above configuration to allow each of the suture carriers to be actuated and driven independently by dividing the deployment controls and the suture carrier drivers into separate left and right hand members. Further, it is possible to utilize a tool that uses only a single suture carrier and guides the carrier through both sides of the wound as opposed to the double suture carrier configuration described above.

Figure 2A:
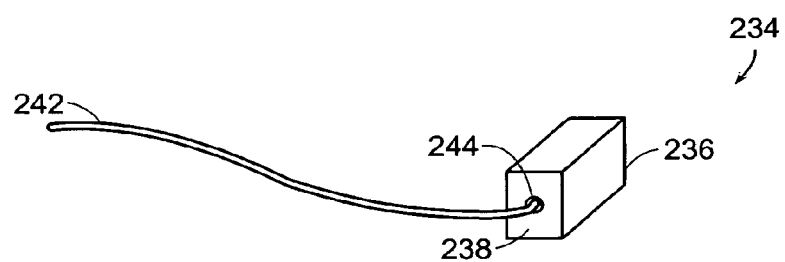
FIGS. 2A-2D and 2F are perspective views of various embodiments of sutures and formed suture tips.

Referring to FIG. 2A, a formed tip 234 (such as the formed tip 6 described above and the one described hereinafter) comprises a body 236 having a shoulder 238. The shoulder 238 is the rear surface of the formed tip body 236 that engages a catch. A length of suture material 242 is inserted into a hole 244 located on the shoulder 238 and attached to the formed tip 234 thereby. The suturing material 242 is attached to the body 236 by any suitable means, such as crimping or adhesive bonding. The rectangular shaped body 236 is merely illustrative, and the shape may be varied to fit a particular application. For example, a simple elongated cylinder or a triangular block may be used, as shown in FIGS. 2B-2E. The formed tip 234 can be manufactured from a plastic, metal, or polymer compound and can be formed by, for example, extrusion, molding, or machining. Furthermore, the type of material(s) used to form the suture is not critical to the present invention, as long as the material(s) used is/are biocompatible. The formed tip 234 of the present invention may be used with any type or size (length, cross-sectional shape) of suture material. The surgeon will select the length, diameter, and characteristics of the suture to suit a particular application.

Various possible formed tips according to the invention are now described with reference to FIGS. 2B-2H.

Figure 2B:
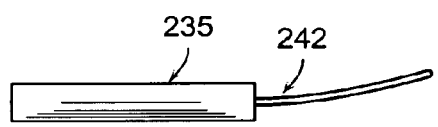
Figure 2C:
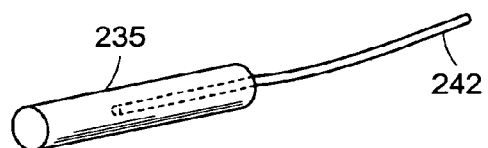

In FIG. 2B, the suture 242 is shown attached to an elongated cylindrically-shaped body 235, which may illustratively be somewhat rigid, at least as compared to the suture 242, to facilitate capture by a catch. As illustrated in FIG. 2C, an end portion of the suture 242 may be molded or otherwise formed within the body 235 of the formed tip.

Figure 2D:
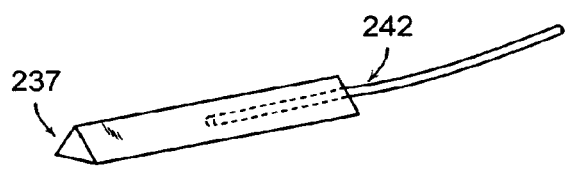
Figure 2E:
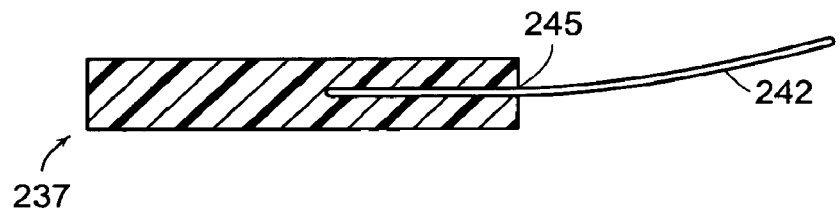
FIG. 2E is a cross-sectional view of one embodiment of a suture and formed tip.

In FIGS. 2D and 2E, the body 237 has a generally triangular cross-sectional shape and is shown attached to the suture 242. It will be appreciated that the suture 242 may be inserted into a mold in which a plastic or plastic-like material of the body 237 is injected. Alternatively, the suture 242 may be held within a hole 245 within the body 237 by adhesive bonding.

Figure 2F:
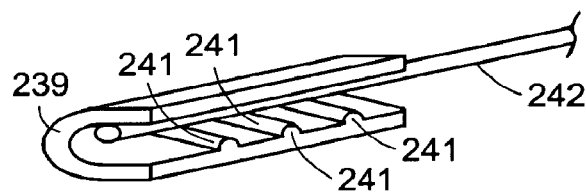
Figure 2G:
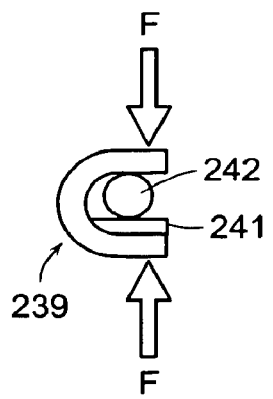
FIGS. 2G and 2H are end views of the embodiment of a suture and formed tip shown in FIG. 2F.
Figure 2H:
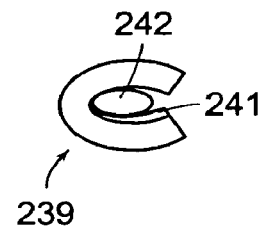

FIGS. 2F-2H show how a body 239 may be clamped downwardly on a suture 242 and welded or otherwise pressure formed and closed to capture the suture 242. The body 239 is an elongated member having a C-shaped cross-section, as shown in FIG. 2F, to receive the suture 242. The body 239 may have a plurality of ridges 241 as shown to grip the suture 242 when the C-shaped body 239 is clamped with forces F as shown in FIG. 2G to produce the cross sectional shape shown in FIG. 2H. Techniques for welding or joining plastic by the application of pressure and energy to capture another material, such as a suture, are well known.

Figure 3A:
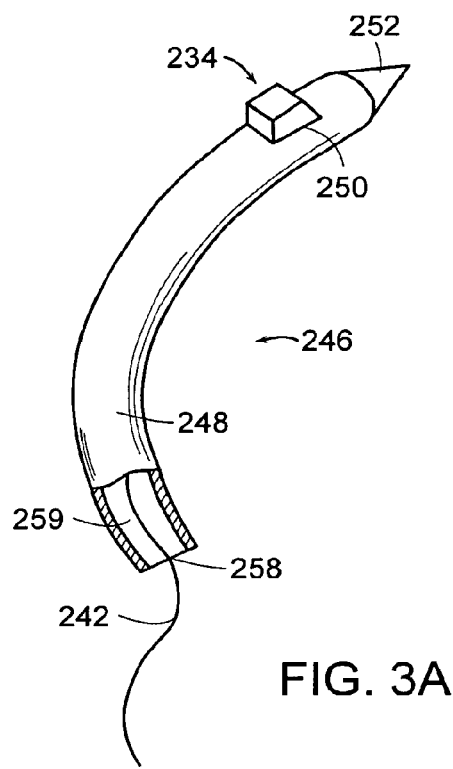
FIG. 3A is a partial-cutaway view of a suture carrier.

Referring now to FIG. 3A, a suture carrier 246 (such as the suture carriers described above and the one described hereinafter) comprises a body 248 defining a lumen 259, a notch 250 to receive a formed tip 234, and a sharpened end 252 for tissue penetration. Forming or machining may be used to fabricate the sharpened end 252. The lumen 259 is in communication with the notch 250 at one end and with an aperture 258 at the other end. The notch 250 is sized and shaped to releasably engage the formed tip 234. A length of suture material 242 attached to the formed suture tip 234 is inserted into the notch 250, through the lumen 259, and out the aperture 258. The attached formed tip 234 is then releasably engaged with the notch 250. Alternatively, the suture carrier 246 can be a solid piece with the suture 242 disposed in a groove in the outer surface of the suture carrier 246.

Figure 3B:
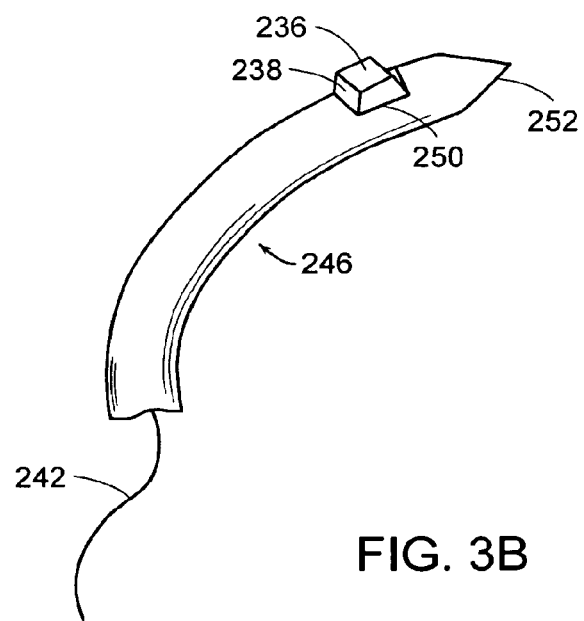
FIG. 3B is an enlarged perspective view of the suture carrier of FIG. 3.

FIG. 3B depicts an enlarged view of the tip of the suture carrier 246. The formed tip 234 is releasably engaged with the notch 250 so that the body 236 protrudes slightly from the notch 250. The rear surface of the body 236, which forms the shoulder 238, faces away from the sharpened tip 252. The formed tip 234 is engaged with the notch 250 such that the body 234 is held in place by frictional forces when the suture carrier 246 is extended forward. The body 236 is released from the notch 250 when the suture carrier 246 is retracted from a catch. The shoulder 238 is dimensioned so as to be retained by the catch when the suture carrier 246 exits the catch. The interaction of the suture carrier 246 and various catches is described in greater detail with respect to FIGS. 4 and 5.

Figure 4:
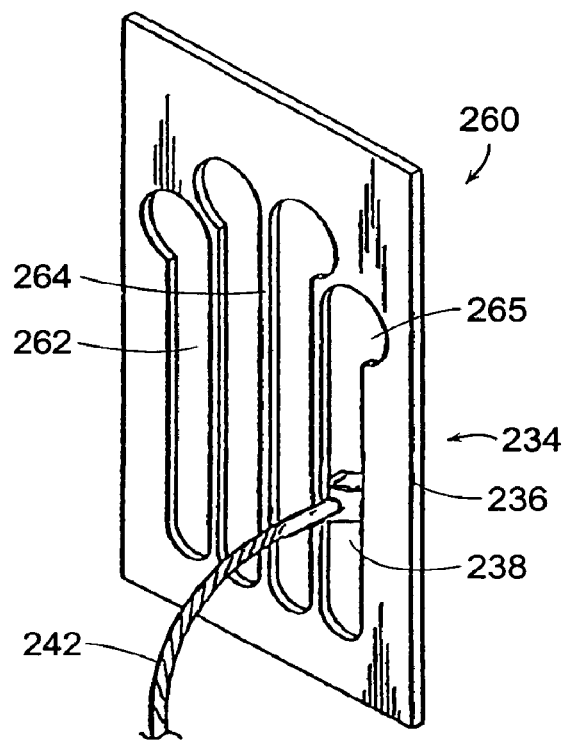
FIG. 4 is a perspective view of a catch and a suture with a formed suture tip.
Figure 5:
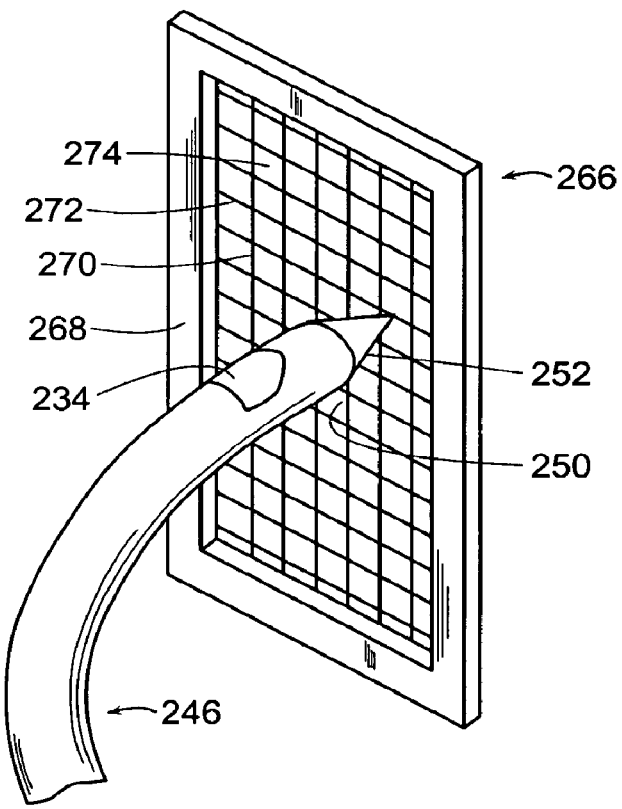
FIG. 5 is a perspective view of an alternate catch mechanism with a suture carrier.

FIGS. 4 and 5 depict alternate catches and illustrate their operation. Referring to FIG. 4, the catch 260 includes openings 262 defined by successive ribs 264. The catch 260 receives a suture carrier 246 (not shown) and a suture 242 with a formed tip 234 through opening 262, the ribs 264 deflect slightly to allow the suture carrier 246 and formed tip 236 to pass through. After the formed tip shoulder 238 has passed the ribs 264 and the suture carrier 246 has been withdrawn, thereby releasing the formed tip 234, the ribs 264 spring back to their original position defining the openings 262. The openings 262 are chosen to be smaller in dimension than the formed tip shoulder 238. This causes the catch 260 to retain the formed tip 234, because due to the flat rear surface of the shoulder 238, the formed tip 236 cannot pass back through an opening 262. When it is necessary to remove the formed tip 234 from the catch 260, it may be moved toward an enlarged portion 265 of opening 262. The enlarged portion 265 is sized to allow the formed tip shoulder 238 to pass through without resistance. The catch 260 is preferably constructed of thin stainless steel of high temper, such as ANSI 301 full hard. The catch 260 may be fabricated by means of stamping, laser machining, or chemical etching.

Referring now to FIG. 5, a catch 266 includes a frame 268 to which is attached a woven mesh 270. Threads 272 creating the woven mesh 270 may be nylon, polyester, or the like woven in a common over/under pattern. The weaving of the threads 272 creates windows 274 in the mesh through which a suture carrier 246 may be passed. The suture carrier 246 is constructed such that the shoulder 238 of the formed tip 234 is larger than the windows 274, or conversely, the windows 274 are chosen to be smaller than the shoulder 238. The sharpened end 252 of the suture carrier 246 pushes the threads 272 aside creating room for the shoulder 238 to pass through the windows 274. Upon withdrawal of the suture carrier 246, the threads 272 return to their original positions and the catch 266 retains the formed tip 234 (once again due to the flat rear surface of the shoulder 238, which is larger than the windows 274).

Figure 6B:
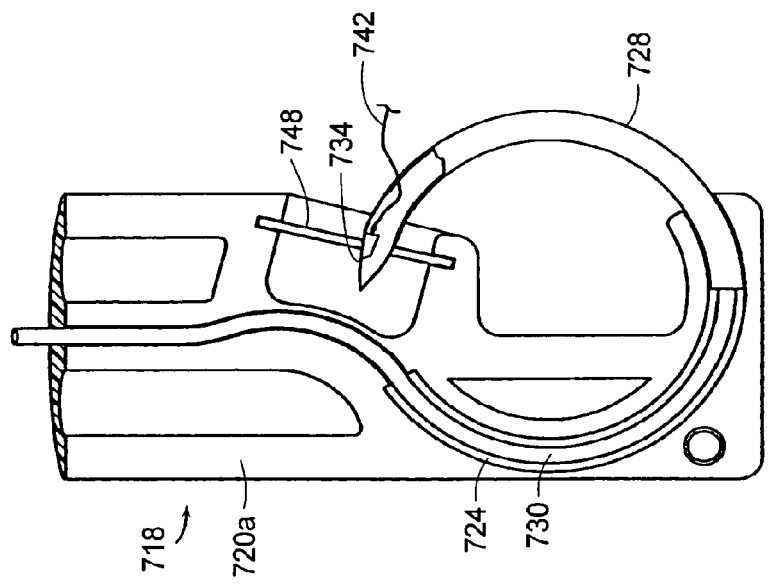
FIGS. 6A and 6B are partial cutaway views illustrating the general structure and operation of one embodiment of a suture delivery and capture system.
Figure 8:
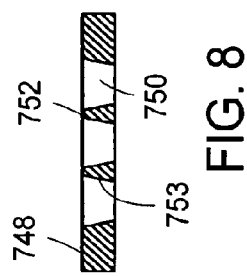
FIG. 8 is a cross-sectional view taken along line 8-8 of FIG. 7.
Figure 7:
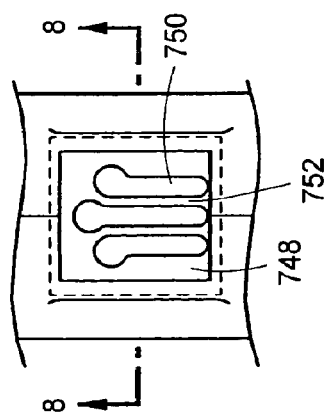
FIG. 7 is a partial side view taken along line 7-7 of FIG. 6A and illustrating the formed suture tip catch.
Figure 6A:
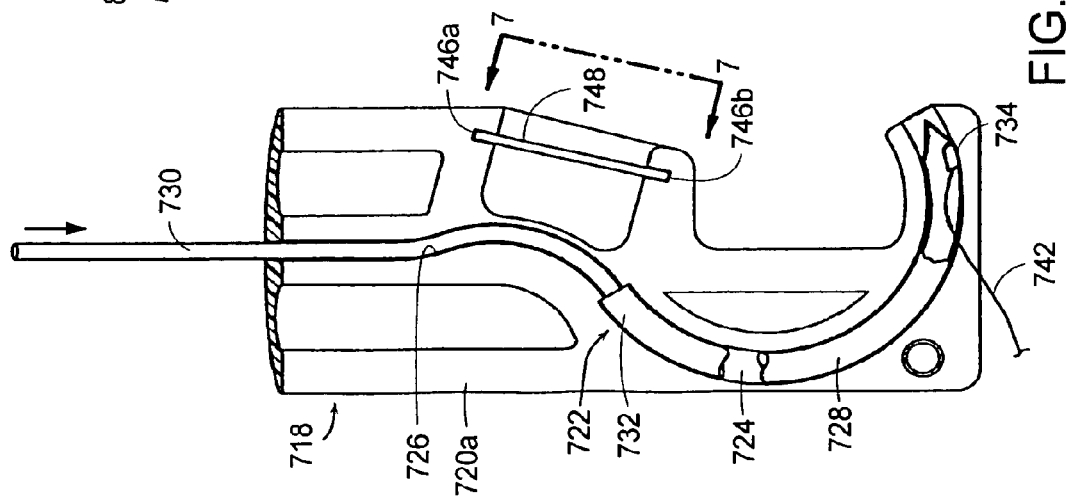

FIGS. 6A and 6B depict one embodiment of a suture carrier and catch system. Referring to FIG. 6A, an elongate body member 718 is formed of two complementary housing halves 720a,b. It is to be understood that for clarity only one of the housing halves 720a of the elongate body member 718 is shown in FIGS. 6A and 6B. The housing halves 720a,b are configured to create a guided pathway 722 that includes a suture carrier channel 724 and a flexible carrier driver guide track 726. A suture carrier 728 and flexible carrier driver 730 are joined at an end 732 of the suture carrier 728. Crimping, welding, adhesive bonding, or various other techniques can accomplish the attachment between the suture carrier 728 and the flexible carrier driver 730 at the end 732. A formed tip 734 and a length of suture material 742 are attached to the suture carrier 728. Further incorporated in the housing halves 720 are a pair of catch pockets 746a,b, which position and retain a catch 748. Referring to FIG. 7, the catch 748 includes openings 750 defined by ribs 752. The configuration and function of the formed tip catch 748 is similar to that described earlier with respect to FIG. 4. When the catch 748 is fabricated by means of chemical etching, the preferred method is to etch from a single side, known in the art as single sided etching. When the catch 748 is etched from a single side, the ribs 752 have a tapered cross-section 753 as shown in FIG. 8. The tapered cross section 753 helps to guide the sharpened end of the suture carrier 728 into the catch openings 750, thereby minimizing the chance of the sharpened end of the suture carrier 728 hitting the top of the ribs 752.

With renewed reference to FIGS. 6A and 6B, the operation of this embodiment will be described. FIG. 6A shows the formed tip 734 loaded into the suture carrier 728, which is depicted in the retracted position. In this position, the body 718 may be passed through a surgical trocar and into a body cavity for operation of the device. As shown in FIG. 6B, as the flexible carrier driver 730 is advanced into the suture carrier channel 724, the suture carrier 728, holding the formed tip 734 and trailing the suture 742, is driven in a semi-circular path that intersects the catch 748. The formed tip 734 is received and retained by the catch 748 in a manner previously described with respect to FIG. 4. The flexible carrier driver 730 may be retracted back into the flexible carrier driver guide track 726, causing the suture carrier 728 to rotate back into the suture carrier channel 724. The instrument may be removed from the surgical trocar, and the process repeated on the other side of the wound.

FIGS. 6C and 6D depict an alternate suture carrier and catch system. Referring to FIG. 6C, an elongate body member 770 is comprised of a pair of complementary housing halves 772a,b. It is to be understood that for clarity only one of the housing halves 772a of the body 770 is shown in FIGS. 6C and 6D. The housing halves 772a,b are configured to create a guided pathway 774 that defines a suture carrier channel 776 and a flexible carrier driver guide track 778. A suture carrier 780 and flexible carrier driver 782 are joined at a saddle 784 of the suture carrier 780. The saddle 784 comprises a channel, groove, or opening formed in the proximate end of the suture carrier 780 into which the flexible carrier driver 782 may enter. Crimping, welding, adhesive bonding, or various other techniques can accomplish the attachment between the suture carrier 780 and the flexible carrier driver 782 at the saddle 784. A formed tip 790 and a length of suture material 794 are attached to the suture carrier 780. Further incorporated in the housing halves 772a,b are a pair of catch pockets 798a,b that position and retain a catch 800. The configuration and function of the catch 800 is similar to that described earlier with respect to FIG. 4. The suture carrier 780 carries the formed tip 790 of the suture through the tissue and into the catch 800 as previously described.

Although the operation of this embodiment is similar to that described in FIGS. 6A and 6B, there are some differences. Referring back to FIGS. 6A and 6B, as the suture carrier 728 approaches the end of its stroke, as illustrated in FIG. 6B, the circumferential length of the suture carrier 728 left inside the suture carrier channel 724 is minimal. This may allow the suture carrier 728 holding the formed tip 734 to drift off of the prescribed arcuate path that terminates in the formed tip catch 748. This drift may allow the sharpened end of the suture carrier 728 to miss the catch 748, causing an incomplete suturing cycle. Therefore, it is desirable to increase the circumferential length of the suture carrier left inside the guide track in order to improve the guidance of the suture carrier.

Accordingly, the embodiment illustrated in FIGS. 6C and 6D equips the suture carrier 780 with the saddle 784. The saddle 784 allows the flexible carrier driver 782 to exit from the suture carrier 780 at a point along the circumference, rather than at a distal end 804. This may be seen to increase the overall arc length of the suture carrier 780 when compared with the suture carrier 728 shown in FIG. 6A. As a result, when the flexible carrier driver 782 is slidably moved in the guided pathway 774, the suture carrier 780 rotates within the suture carrier channel 776 such that when the formed tip 790 enters the catch 800, a significantly larger portion of the suture carrier 780 is still captured within the suture carrier channel 776. This may provide additional guidance to the suture carrier 780 as it penetrates tissue. This geometry may also allow for a longer stroke length and greater tissue bite.

Figures 9A, 9B:
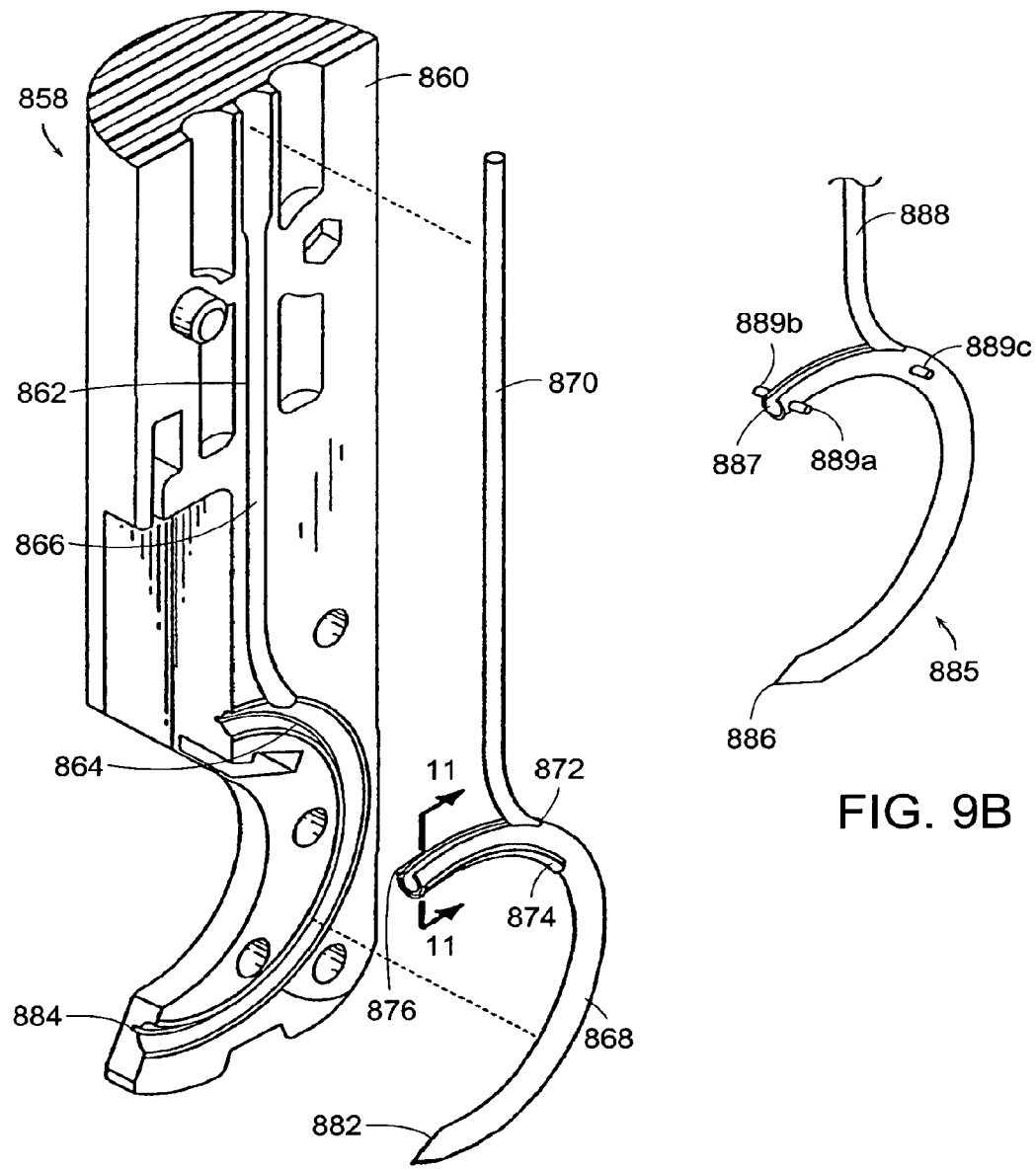
FIG. 9A is an exploded illustrating the general structure of an alternate embodiment of the suture carrier and guide track.
FIG. 9B is a perspective view illustrating the general structure of an alternate embodiment of the suture carrier of FIG. 9A.

Referring to FIG. 9A, the distal end of an elongate body 858 is comprised of a pair of complementary housing halves 860a,b. It is to be understood that for clarity only one of the housing halves 860a of the body 858 is shown in FIG. 9A. The housing halves 860a,b are configured to create a guided pathway 862 that defines a suture carrier channel 864 and a flexible carrier driver guide track 866. A suture carrier 868 includes a saddle 872, to which is attached a carrier bearing 874. The saddle 872 comprises a channel, groove, or opening formed in the proximate end of the suture carrier 868 into which the flexible carrier driver 870 may enter.

The construction of the suture carrier may be best understood by referring to FIG. 11A, where a cross-sectional view shows the suture carrier 868 and the carrier bearing 874. The carrier bearing 874 further includes bearing wings 876a,b. The carrier bearing 874 may be joined by welding, adhesive bonding, or the like to the suture carrier 868.

The suture carrier 868 may also be formed by another method. FIG. 11B shows a cross-sectional view of a suture carrier 878 that has been formed out of, for example a 17-4 stainless steel alloy by a process called metal injection molding. This process allows the suture carrier 878 to be formed in a monolithic fashion such that the suture carrier 878, bearing wings 880a,b, and saddle are formed as one piece. Other processes such as die casting, investment casting, or powdered metal could also be used to create a monolithic suture carrier 878.

Another embodiment of the suture carrier, indicated generally at 885 in FIG. 9B, includes a sharpened end 886 at the distal end adapted to penetrate tissue and a groove 887 at the proximal end adapted to contain a flexible suture driver 888 as previously described. A series of pins 889a,b, c, d are attached to the sides of the suture carrier 885. The pins 889a,b, c, d are dimensioned to be slidably disposed within the groove 884 in the suture carrier channel 864, and to provide guidance and stability to the suture carrier 885 in a fashion similar to that described with reference to FIG. 9A below.

Referring again to FIG. 9A, the suture carrier 868 and flexible carrier driver 870 are joined as previously described at saddle 872 of the suture carrier 868, which incorporates bearing wings 876. The suture carrier 868 has a sharpened distal end 882 adapted to penetrate tissue as previously described in other embodiments. Alternatively, the suture carrier 868 may include an aperture located at its distal end for receiving a surgical needle, the needle being permanently attached to the suture carrier 868. The needle includes a sharpened distal tip and a notch for holding a formed suture tip. The surgical needle can be permanently attached to the suture carrier 868 by welding, chemical bonding, or similar technique. In this embodiment, the suture carrier guide track 864 further incorporates a groove 884 adapted to receive the bearing wings 876a,b. FIG. 12 depicts a detailed cross-sectional view of the groove 884 and the bearing wings 876. FIG. 13 depicts a detailed cross-sectional view of the suture carrier guide track 864 and illustrates an area of the suture carrier 868 and of the suture carrier guide track 864 where there are no bearing wings 876. It should be understood that the cross-section shown in FIG. 13 of the suture carrier 868 could be of solid material instead of tubular material if the cross-section were illustrating a monolithic part, such as suture carrier 878. It may also be understood from the foregoing illustrations, that the width and depth of the bearing wings 876a,b shown in FIG. 11A and the bearing wings 880a,b shown in FIG. 11B are not to be taken as literal illustrations of the physical dimensions of those features, as the width and depth may be varied in order to achieve more or less guidance and bearing surface area as the designer deems appropriate.

The operation of the embodiment described in FIGS. 9A through 13 is identical to that previously described in FIGS. 6C and 6D, with the exception that the bearing wings 876a,b are adapted to rotationally slide in the grooves 884a,b of the housing halves 860a,b. This provides axial and torsional guidance and resistance to deflection of the suture carrier 868 from the anticipated path. Performance improvements over the embodiment described in FIGS. 6C and 6D relate primarily to an increased ability to torque and/or lift the device while the suture carrier is exposed to the tissue to be sutured.

The preferred material for the flexible carrier driver 870 is an alloy of nickel and titanium known in the art as nitinol. This material has both austenitic and martensitic forms, and can be alloyed to exhibit properties of both forms as the material moves through a transition temperature that can be varied. The martensitic form of the alloy, when processed into, for example wire, has a lead-solder like consistency and easily deflects plastically to a certain point, beyond which a considerable amount of force is necessary to cause further deflection. This elastic behavior is what allows the material to be both flexible and exhibit high column strength when properly constrained. Thus, the flexible carrier driver 870 is constrained in a track that allows it to be moved axially, but constrains its deflection off-axis.

Another embodiment of the invention is shown in FIGS. 14-18. This embodiment of the present invention is particularly well suited for, e.g., the fixation of sutures to the Cooper's ligament during the performance of a Burch bladder neck suspension via a transvaginal approach. As will become apparent, this embodiment includes features for limiting the depth of the sharpened end penetration for placing sutures in, for example, ligaments lying directly on bone, and for accommodating the anatomy of, for example, the female pelvis.

Figure 14:
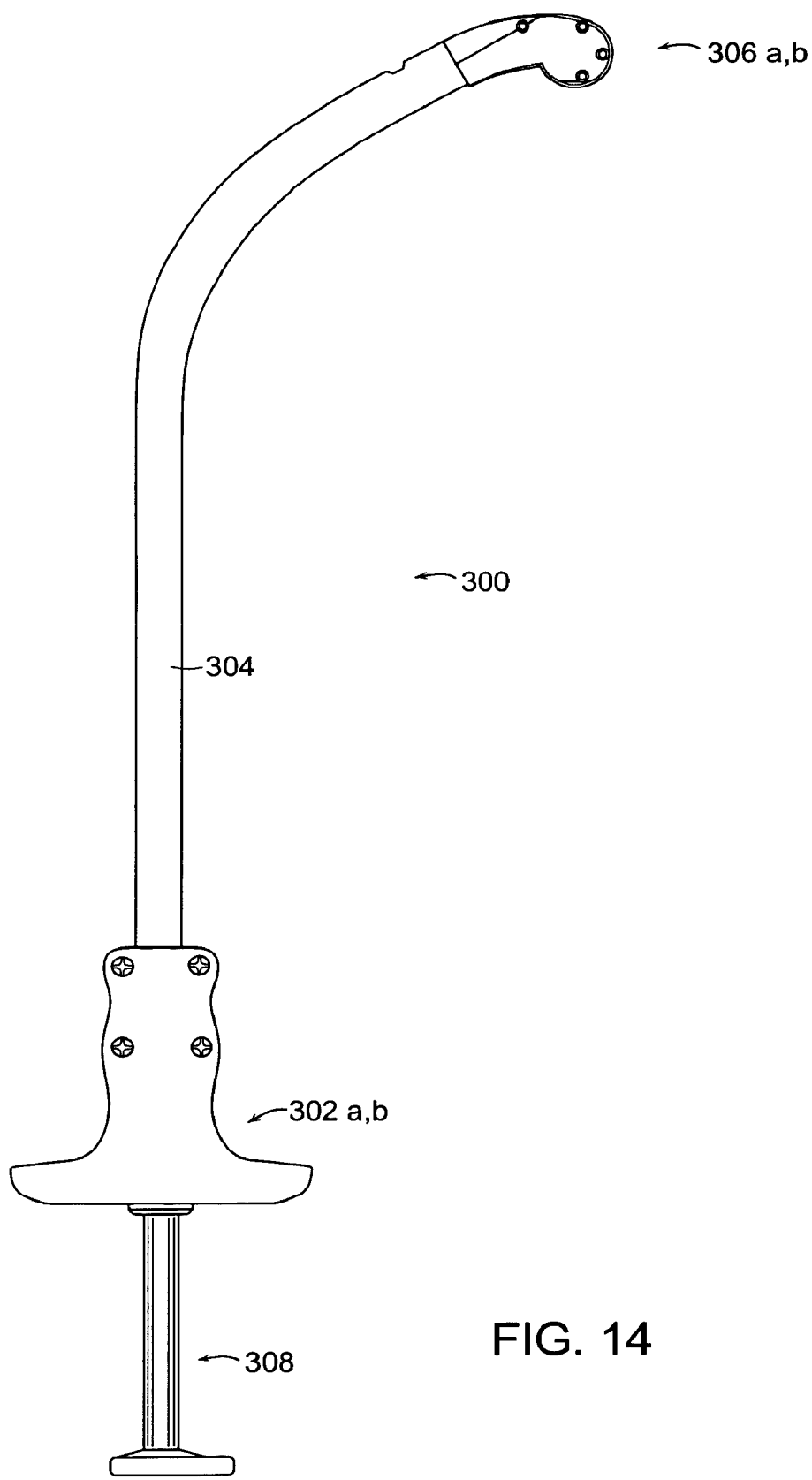
FIG. 14 is an elevation of another embodiment of the present invention.
Figures 15, 16:
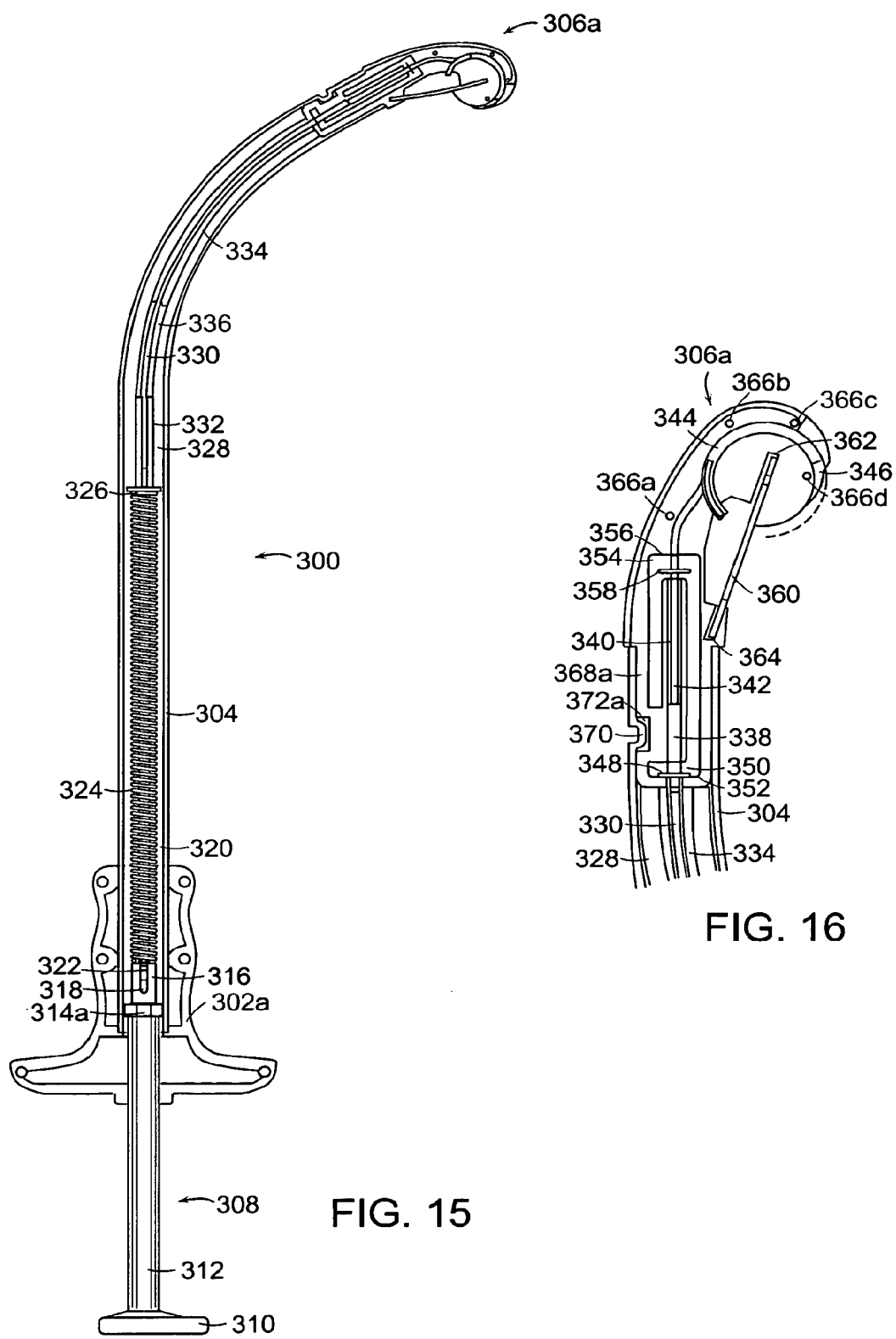
FIG. 15 is a cutaway view illustrating the general internal structure of the embodiment shown in FIG. 14.
FIG. 16 is a cutaway view of the head of the embodiment shown in FIGS. 14 and 15.

FIG. 14 depicts a suturing instrument 300 including a pair of handles 302a,b, an elongate body 304, distal tips 306a,b, and an actuator button 308. FIG. 15 depicts the suturing instrument 300, the handle 302a, the elongate body 304, the distal tip 306a, and the actuator button 308 in cross-section. The actuator button 308 includes a button head 310, a button shaft 312, a series of button bearing surfaces 314a,b, c, d, a button end 316, and a hole 318. The button bearing surfaces 314a,b,c,d ride along a cylindrical surface 320 that is formed by the inside diameter of the elongate body 304. A wireform 322 is inserted into the hole 318, coupling it to the actuator button 308. A spring 324 encircles the wireform 322, abuts the button end 316, and is compressed between the button end 316 and a spring washer 326. The spring washer 326 is seated upon a center tube 328. The center tube 328 is housed by the cylindrical surface 320 and is constrained at the distal end by the distal tip 306. A pusher wire 330 is attached to the wireform 322 by means of a weld, a coupling, adhesive, or other means, and is slidably disposed within a proximal guidance sleeve 332 and a distal guidance sleeve 334, said sleeves 332, 334 being disposed within a cylindrical surface 336 formed by the inside diameter of the center tube 328.

The pusher wire 330 is preferably constructed of nitinol wire, so chosen as previously discussed for its combination of properties that allow for bendability and high column strength when constrained. The constraints in this construction are provided by the proximal guidance sleeve 332 and the distal guidance sleeve 334.

FIG. 16 depicts the distal end of the suturing device 300. For the purposes of clarity, only one of the distal tips 306a is shown and cross-sectional representations of the center tube 328, the distal guide tube 334, and the elongate outer tube 304 are shown. The pusher wire 330 is attached by welding or other means to a coupling 338, which is slidably disposed within a track 340. The coupling 338 is also attached to a carrier wire 342, which by virtue of its attachment to the coupling 338, is also slidably disposed within the track 340. The carrier wire 342 is attached to a suture carrier 344 by welding or other means. The carrier 344 is rotatably and slidably disposed within a suture carrier channel 346 molded into the distal tip 306. The relationship between the carrier wire 342, the carrier 344, and the channel 346 is similar to that previously described in FIGS. 9-13. The coupling 338 abuts a backstop washer 348 that is slidably disposed about the pusher wire 330, and constrained within a pocket 350. The pocket 350 includes a back wall 352, against which the backstop washer 348 rests.

The track 340 terminates distally in a pocket 354 that includes a wall 356. A downstop washer 358 is slidably disposed about the carrier wire 342 and constrained within the pocket 354. Positioned at the terminus of the path of the carrier 344 is a catch 360 that is held distally in a pocket 362 and proximally in a pocket 364. The catch 360 is similar in construction and function to the catch described with respect to FIGS. 4, 7, and 8. The distal tips 306a,b are held together by rivets placed in rivet holes 366a,b,c,d and by tip shafts 368a,b being inserted into the cylindrical surface 320, which is the inside diameter of the elongate body 304. A depression 370 in the elongate body 304 may be formed by mechanical means such as striking with a pin or forming with a die. The depression 370 is engaged in a rotation pocket 372a,b that is formed as a feature of the distal tips 306a,b, and will be further described with respect to FIGS. 18A-18B.

FIGS. 17A-17D depict a sequence of operation of the suturing instrument shown in FIGS. 14-16. Although this description relates to a specific application, i.e., the performance of a Modified Burch bladder neck suspension via a transvaginal approach, it is to be understood that the principles and construction herein described may be applied to other areas of the human body, and for other procedures requiring suturing body structures, such as ligaments that are in direct communication with bone. FIG. 17A depicts a cross-sectional view of the distal tip of the suturing device 300. The suturing device 300 is shown with a suture 374 attached to a suture formed tip 376 in a manner similar to that described with respect to FIG. 2 and is shown loaded into the suture carrier 344 in preparation for actuation. The suturing device 300 has been placed against a ligament 378 that lies directly on a bone 380. Referring to FIGS. 15 and 17A, it may be seen that the pusher wire 330 is held in tension by the spring 324, as the coupling 338 shown in FIG. 17A abuts the backstop washer 348 that is held against the back wall 352, positioning the suture carrier 344 in its retracted position.

As those skilled in the art will appreciate, it can be quite difficult to drive a suture through a ligament that lies directly on bone, as the bone's density typically does not allow a suture needle to penetrate it. Thus a skimming path should be taken to avoid hitting bone, but ensuring good penetration of the ligament and a subsequent "good bite" of tissue. In the case of the Cooper's ligament that is the focus of the anterior fixation point for the Modified Burch bladder neck suspension procedure, the difficulty in placing those sutures is directly attributable to the ligament lying on the bone and the problems with exposure of the ligament to the surgeon.

Again referring to FIG. 15, and now FIG. 17B, the actuator button 308 is depressed by pushing on button head 310, which via attachment to the wireform 322 is attached to pusher wire 330, which moves coupling 338 along track 340 while concomitantly moving the carrier wire 342, which slidably and rotatably moves the suture carrier 344 in the channel 346 and drives the sharpened end of the suture carrier 344 into the ligament 378. The suture carrier 344 skims or slides along the surface of the bone 380, maximizing the depth of penetration, but not digging in or penetrating the bone surface.

Referring now to FIG. 17C, the coupling 338 reaches a point in its travel along the track 340 where it pushes the downstop washer 358 against the wall 356 of the pocket 354. This action limits the outward travel of the suture carrier 344 to prevent overdriving and reduces or eliminates the possibility of expelling the suture carrier 344 from the distal tip 306. The suture carrier 344 drives the formed tip 376 and attached suture 374 through ligament 378 and into the catch 360, where it is received and retained in a manner previously described. As the button 308 is released, the spring 324 urges the button 308 proximally, moving the pusher wire 330, the coupling 338, the carrier wire 342, and the suture carrier 344 along with it to the position shown in FIG. 17D, where the backstop washer 348 arrests the proximal movement in a manner previously described, leaving the formed tip 376 in the catch 360 and the suture 374 driven through the ligament 378.

Figure 10:
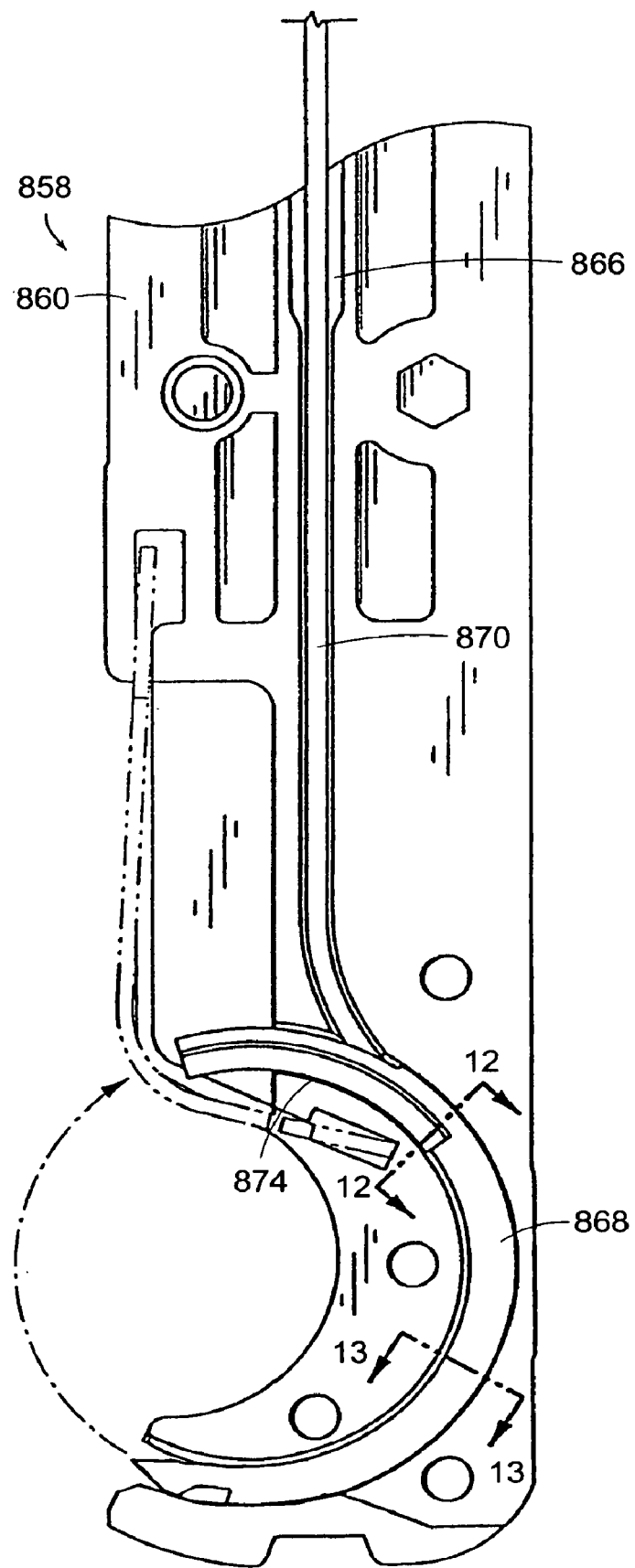
FIG. 10 is a cross-sectional view illustrating the relationship between the suture carrier and guide track.

A variation of this embodiment can be seen with respect to FIGS. 10 and 16. In the embodiment shown in FIG. 10, the path of the suture carrier 868, illustrated by a phantom line in FIG. 10, exits the housing 860 in a direction that is substantially perpendicular to the surface of the housing 860 and presents an opportunity for the suture carrier 868 to be driven directly into the tissue surface placed against the exit port. Thus, if there were bone immediately underlying that tissue, this would allow the sharpened end of the suture carrier 868 to be driven directly into bone. In the embodiment shown in FIG. 16, a phantom line illustrates a different type of carrier path. In this embodiment, the carrier path exits the distal tip 306 in a direction that approaches being substantially tangential to the surface of the distal tip 306. This substantially tangential exit path allows this instrument to achieve the skimming tissue bite referred to earlier. As shown in FIGS. 17A-17D, when the surface surrounding the exit port of this device is placed next to a tissue surface, the sharpened end of the suture carrier 344 takes a skimming tissue bite, thereby minimizing any possible penetration of bone underlying the tissue.

Another aspect of this embodiment which is advantageous to the function of the device is the ability to rotate the distal tip 306 of the instrument relative to the elongate body 304, thereby allowing the instrument to conform to the contours of, for example, the pelvic brim. This is accomplished by incorporating the construction illustrated in FIGS. 18A and 18B. For clarity, the elongate body 304 has been shown in partial cross-section so that the depression 370 may be seen to engage the rotation pockets 372a,b. This engagement couples the distal tips 306a,b to the elongate body 304, as previously described, and also allows the assembly of the distal tips 306a,b to be rotated axially along the cylindrical surface 320.

Figure 19A:
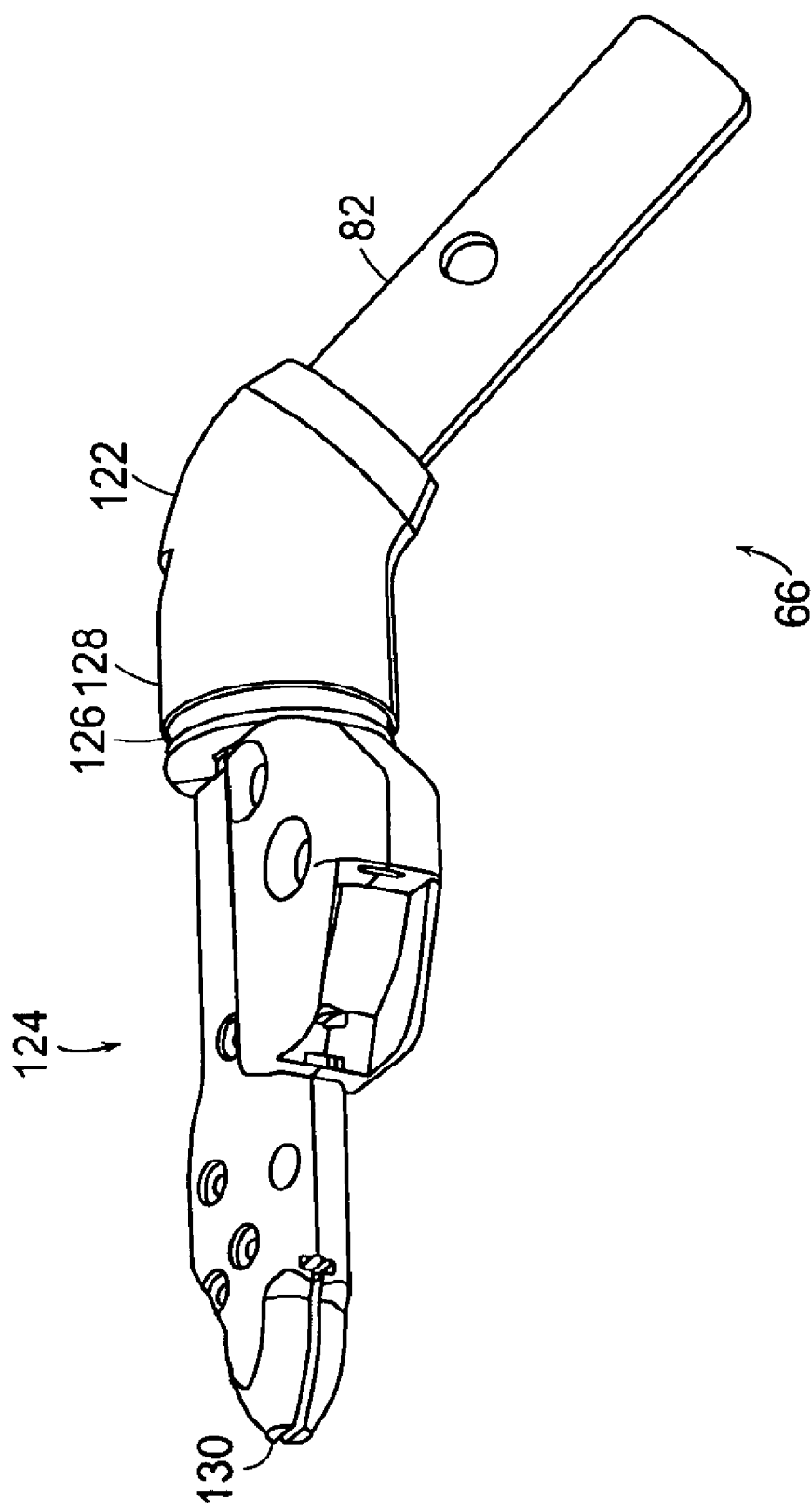
FIGS. 19A-19C are perspective views of one embodiment of a suturing instrument of the invention featuring an elbow-shaped, elongated body member with a rotatable head shown in various rotated positions.
Figure 19B:
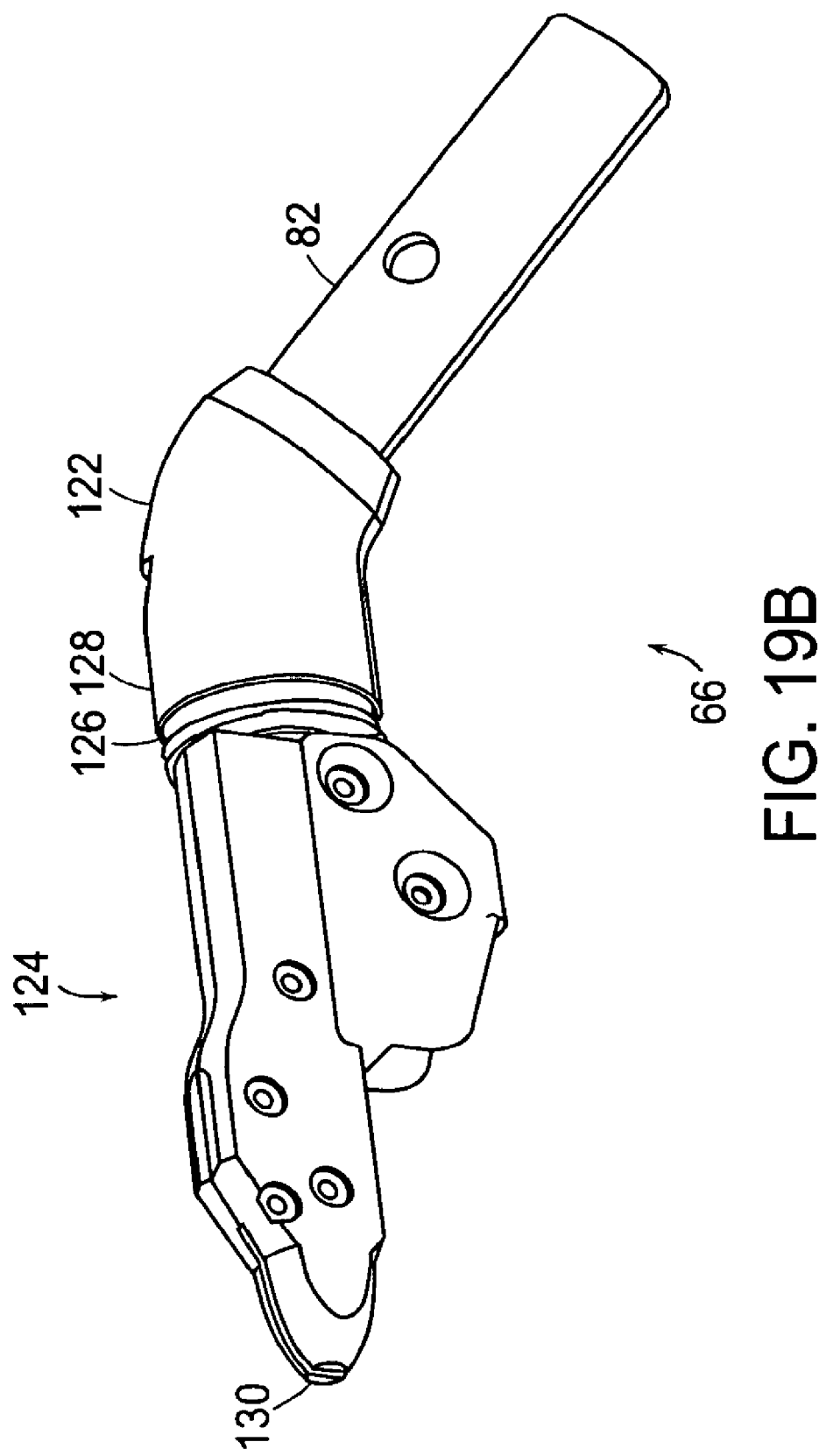
Figure 19C:
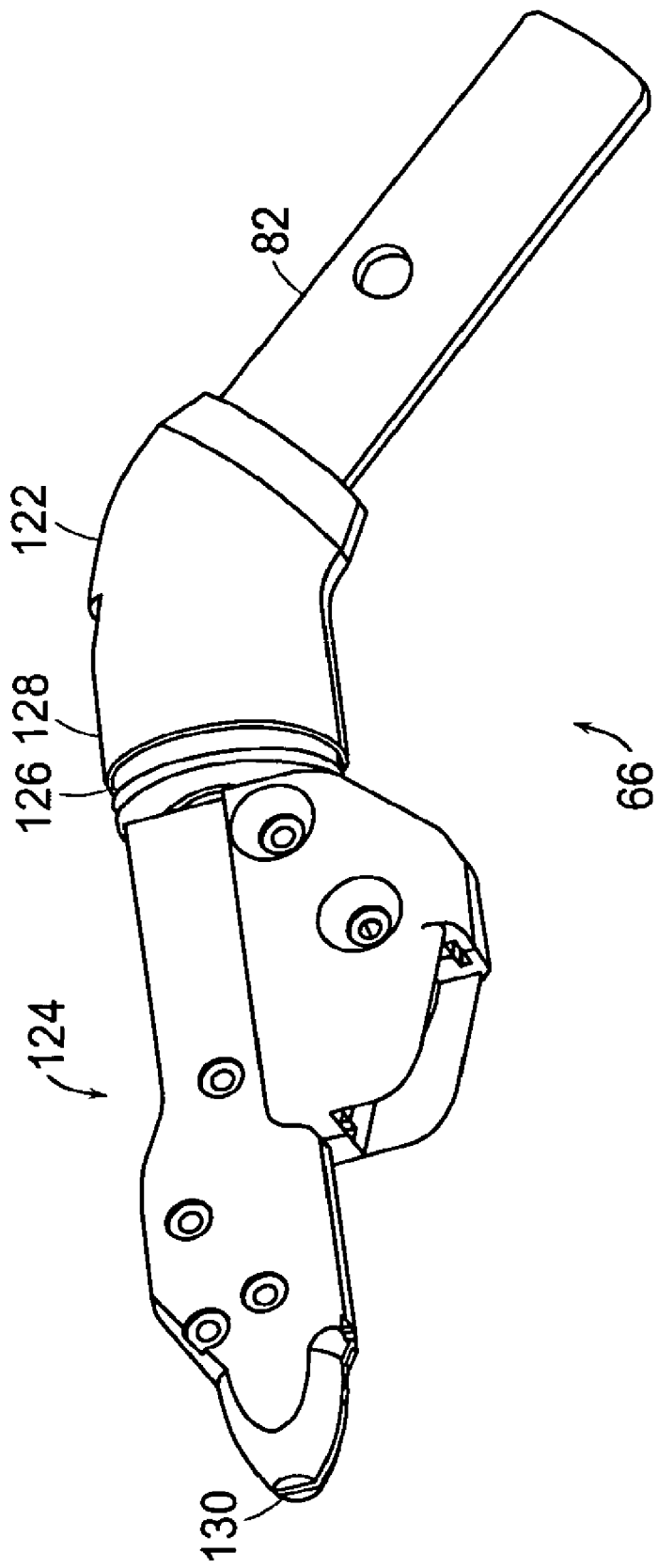

In yet another embodiment, the instrument can be adapted to facilitate access into the abdominal cavity and the placement of suture(s) radially in a body lumen. Such instrument may be particularly useful where anastomosis is required such as urethral anastomosis following radical prostatectomy or in blood vessel or bowel anastomosis. Referring to FIGS. 19A-19C, the suturing instrument 66 includes an elongated body member 82 and a rotatable head 124. The elongated body member 82 can include an elbow 122 (or bend). The head 124 rotates by angular increments. The elongated body member 82 includes an engaging element located at its distal end 128. The head 124 includes an engaging element located at its proximal end 126 for mating with the engaging element of the elongated body member 82. The head 124 includes a dilator cap or a bullet-shaped end at the distal end 130 of the head 124 to maintain the urethra or any other body lumen in a dilated configuration. The rotation of the head 124 is performed manually between each application of a suture in a body lumen and before reloading with the needle and suture to permit application of a series of sutures along the circumference of the lumen, at incremental angular positions that can be as small as 10°. The embodiment of the suturing instrument featuring an elbow and rotatable head is particularly adapted to perform suturing after removal of the prostate to connect the bladder to the urethra or generally following any other type of resection.

Figure 19D:
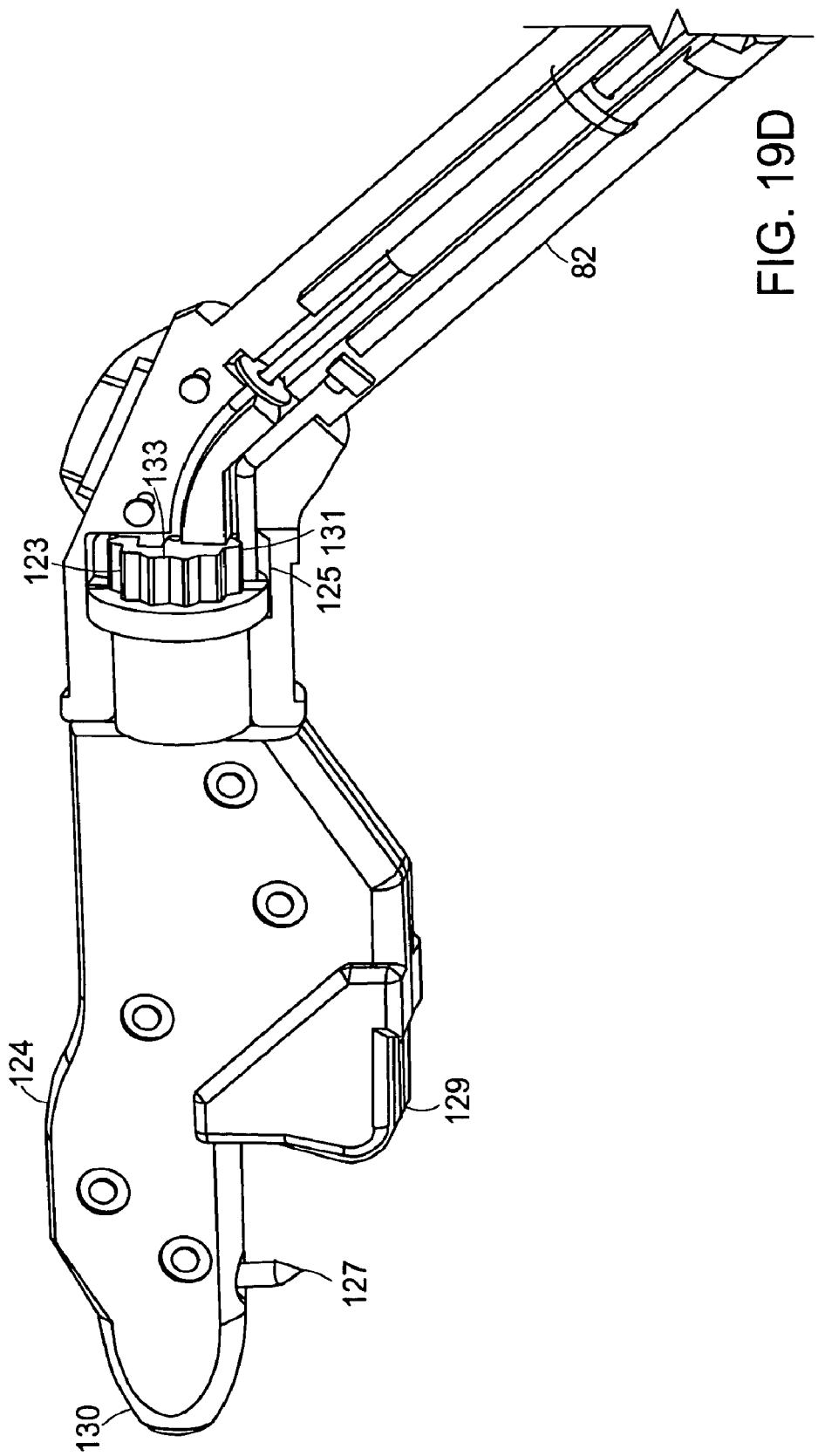
FIGS. 19D-19F are partial-cutaway views illustrating some details of the rotatable head shown in FIGS. 19A-19C and featuring a suture carrier, a catch, and engaging elements.
Figure 19E:
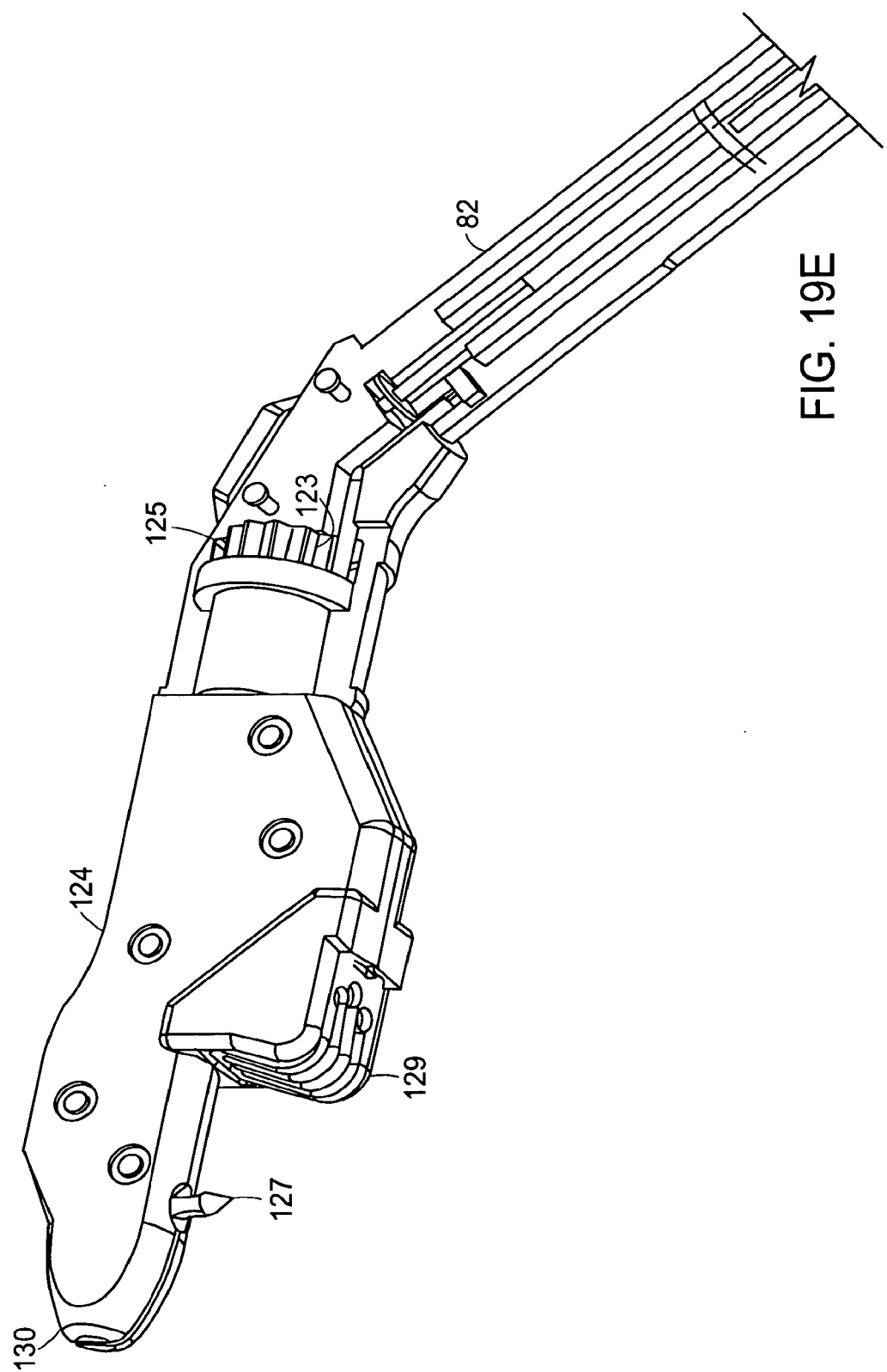
Figure 19F:
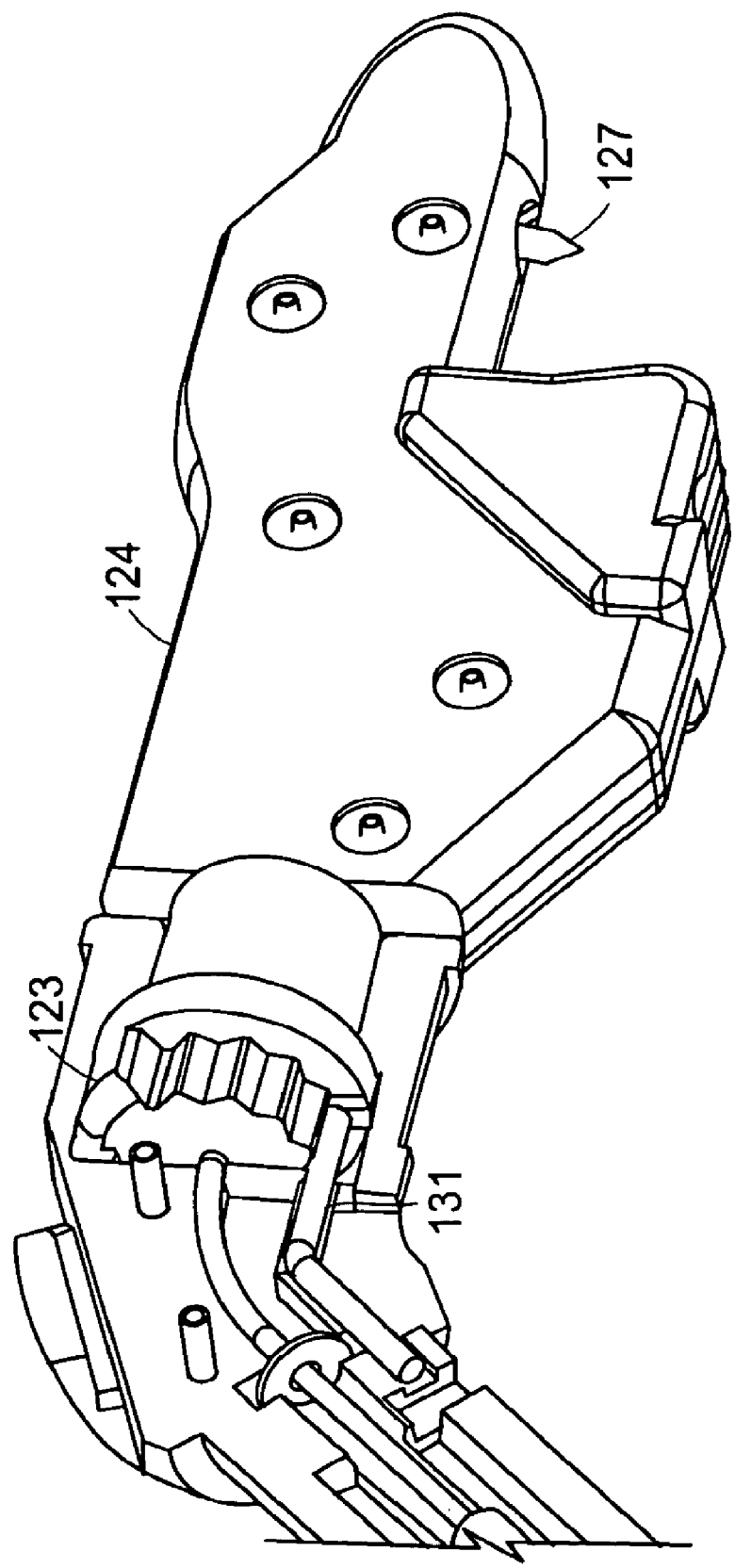

In one embodiment, the rotatability of the head 124 is accomplished with the structure depicted in FIGS. 19D-19F. The head 124 includes an engaging element with a male configuration 123. The male configuration 123 includes a series of fluted cuts 133 located along 330° of its perimeter. The male configuration 123 includes a stop to prevent the head 124 from rotating 360°. The elongated body member 82 includes an engaging element with a female configuration 125 and a flexible detent 131. The female configuration 125 is a substantially circular recess with the flexible detent 131 mounted within the elongated body member 82 and protruding into the substantially circular recess. The flexible detent 131 can be a length of spring wire or a pin and can be made of nitinol. The head 124 can be positioned by rotating the male configuration 123 engaging element with respect to the female configuration 125 engaging element, deflecting the flexible detent 131, and then allowing the flexible detent 131 to mechanically engage the fluted cut 133 which corresponds to the desired angular orientation. The head can be positioned in angular increments of 30°. In addition, the head 124 depicted in FIGS. 19D-19F includes a suture carrier 127 and a catch mechanism 129, which perform substantially the same and are constructed substantially the same as the prior-described suture carriers and catches.

Having described certain embodiments of the invention, it will be apparent to those of ordinary skill in the art that other embodiments incorporating the concepts disclosed herein can be used without departing from the spirit and the scope of the invention. Accordingly, the described embodiments are to be considered in all respects only as illustrative and not restrictive.

What is claimed is:

1. A medical device, comprising:
an elongate body member including a distal portion that defines an internal curved carrier channel and an internal driver guide track; and
a suture deployment system including a curved suture carrier and a carrier driver, the curved suture carrier includes a sharpened distal end for penetrating tissue of a patient, the curved suture carrier is disposed entirely within the carrier channel when the curved suture carrier is in a retracted position and the curved suture carrier is disposed at least partially outside of the carrier channel when the curved suture carrier is in a deployed position, the carrier driver moves through the guide track and into the carrier channel as the curved suture carrier is moved from the retracted position to the deployed position, the carrier driver is attached to the curved suture carrier at a point along the circumference of the curved suture carrier and not at a distal end of the curved suture carrier such that when the curved suture carrier is fully deployed a sufficient portion of the curved suture carrier remains in the carrier channel which helps to guide the curved suture carrier and keep it from drifting off of a prescribed arcuate path as the curved suture carrier is moved from the retracted position to the fully deployed position.

2. The device of claim 1 further comprising a catch disposed to receive at least the sharpened distal end of the curved suture carrier when the curved suture carrier is in the fully deployed position.

3. The device of claim 2 wherein the catch defines at least one opening for receiving at least the sharpened distal end of the curved suture carrier.

4. The device of claim 3 wherein the at least one opening expands in response to receiving at least the sharpened distal end of the curved suture carrier.

5. The device of claim 1 further comprising a suture with a formed suture tip and wherein the curved suture carrier defines a notch for holding the formed suture tip.

6. The device of claim 5 wherein the formed suture tip comprises a plastic, metal, or polymer compound.

7. The device of claim 5 wherein the former suture tip is formed by extrusion, molding, or machining.

8. The device of claim 5 further comprising a catch disposed to receive at least the sharpened distal end of the curved suture carrier when the curved suture carrier is in the fully deployed position, the catch also disposed to receive the formed suture tip when the curved suture carrier is in the fully deployed position and to retain the formed suture tip upon return of the curved suture carrier to the retracted position.

9. The device of claim 8 wherein the formed suture tip is released from the notch upon retraction of the curved suture carrier from the catch.

10. The device of claim 1 wherein a proximal end of the suture deployment system is coupled to an actuator.

11. The device of claim 1 wherein the curved suture carrier comprises a stainless steel alloy.

12. The device of claim 1 wherein the curved suture carrier is formed by metal injection molding, die casting, investment casting, or powdered metal.

13. The device of claim 1 wherein the curved suture carrier is monolithic.

14. The device of claim 1 wherein the carrier driver is flexible.

15. The device of claim 1 wherein the carrier driver comprises an alloy of nickel and titanium.

16. The device of claim 1 wherein the carrier driver is flexible and also exhibits high column strength when moved axially within the guide track.

* * * * *